US010195368B2

(12) United States Patent
Wang et al.

(10) Patent No.: US 10,195,368 B2
(45) Date of Patent: Feb. 5, 2019

(54) HANDHELD HIGH FREQUENCY ULTRASONIC NEBULIZER FOR WHOLE RESPIRATORY TRACT DRUG DELIVERY

(71) Applicants: CHANGZHOU ZHENGYUAN MEDICAL TECHNOLOGY CO., LTD., Changzhou, Jiangsu (CN); GUANGZHOU NANOTIDES PHARMACEUTICALS CO., LTD., Guangzhou, Guangdong (CN)

(72) Inventors: Cheng Wang, Changzhou (CN); Patrick Y. Lu, Guangzhou (CN); Chuntian Lu, Guangzhou (CN); Songlin Jiang, Changzhou (CN); Shenggao Tang, Guangzhou (CN); Tao Yuan, Changzhou (CN)

(73) Assignees: CHANGZHOU ZHENGYUAN MEDICAL TECHNOLOGY CO., LTD., Changzhou (CN); GUANGZHOU NANOTIDES PHARMACEUTICALS CO., LTD., Guangzhou (CN)

( * ) Notice: Subject to any disclaimer, the term of this patent is extended or adjusted under 35 U.S.C. 154(b) by 563 days.

(21) Appl. No.: 14/891,890

(22) PCT Filed: Sep. 25, 2014

(86) PCT No.: PCT/CN2014/087366

§ 371 (c)(1),
(2) Date: Nov. 17, 2015

(87) PCT Pub. No.: WO2015/103891

PCT Pub. Date: Jul. 16, 2015

(65) Prior Publication Data

US 2016/0279352 A1 Sep. 29, 2016

(30) Foreign Application Priority Data

Jan. 13, 2014 (CN) .......................... 2014 1 0013105

(51) Int. Cl.
*A61M 11/00* (2006.01)
*A61M 15/00* (2006.01)
(Continued)

(52) U.S. Cl.
CPC ......... *A61M 11/005* (2013.01); *A61M 11/003* (2014.02); *A61M 15/0085* (2013.01);
(Continued)

(58) Field of Classification Search
CPC A61M 11/00; A61M 11/005; A61M 15/0085; A61M 15/0086; A61M 15/008;
(Continued)

(56) References Cited

U.S. PATENT DOCUMENTS 4,976,259 A * 12/1990 Higson ................ A61M 11/005 128/200.14
5,908,158 A * 6/1999 Cheiman ............. B05B 17/0615 128/200.16

(Continued)

FOREIGN PATENT DOCUMENTS

CN 2137964 Y 7/1993
CN 2232326 Y * 8/1996 ............... B06B 1/06

(Continued)

OTHER PUBLICATIONS

Omron MicroAir Handheld Ultrasonic Portable Nebulizer, retrieved from the WayBack Machine: http://www.allergyasthmatech.com/P/Omron_MicroAir_Handheld_Ultrasonic_Portable_Nebulizer/733 Available on: Mar. 7, 2012.*

(Continued)

*Primary Examiner* — Scott Medway
*Assistant Examiner* — Jacqueline Pinderski
(74) *Attorney, Agent, or Firm* — Oliff PLC

(57) ABSTRACT

A handheld high frequency ultrasonic atomizing device for delivering drugs to whole respiratory tract comprising a
(Continued)

shell with an air inlet and a lid with a spray nozzle. A drug cup with a piezoelectric transducer and a hood with a spray outlet are provided within the shell. The components of piezoelectric ceramic transducer are as follows (mass percentage): lead tetraoxide 63.3-68.3%, zirconium dioxide 14.2-15.3%, titanium dioxide 8.1-9.5%, strontium oxide 4.6-5.2%, iron sesquioxide 1.5-1.8%, stannic oxide 1.0-1.4%, manganese dioxide 0.3-1.1%, cerium sesquioxide 0.5-0.8%, columbium pentoxide 0.4-0.8% and zinc oxide 0.3-0.7%. This device is small in size, with low power consumption and lower cost, and is able to produce mist with small particle size. The device can efficiently deliver drug liquid into the whole respiratory tract, especially down to the lower respiratory tract and pulmonary alveoli through carrying drug molecules in mist particles.

12 Claims, 8 Drawing Sheets

(51) Int. Cl.
*A61M 16/06* (2006.01)
*A61M 16/00* (2006.01)

(52) U.S. Cl.
CPC ..... *A61M 15/0021* (2014.02); *A61M 16/0066* (2013.01); *A61M 16/06* (2013.01); *A61M 2205/3386* (2013.01); *A61M 2205/8206* (2013.01)

(58) Field of Classification Search
CPC ......... B05B 17/00; B05B 17/04; B05B 17/06; B05B 17/0607; B05B 17/0638; B05B 17/0646; B05B 17/0661
See application file for complete search history.

(56) References Cited

U.S. PATENT DOCUMENTS

| | | | | |
|---|---|---|---|---|
| 6,283,118 | B1 * | 9/2001 | Lu | A61M 11/005 128/200.16 |
| 2007/0295328 | A1 | 12/2007 | Raghuprasad | |
| 2008/0245362 | A1 * | 10/2008 | Moessis | A61M 15/0085 128/200.16 |
| 2010/0083956 | A1 * | 4/2010 | Fukumoto | A61M 15/0085 128/200.14 |
| 2014/0083174 | A1 * | 3/2014 | Reboud | H01J 49/165 73/61.59 |
| 2014/0216443 | A1 * | 8/2014 | Hu | A61M 15/0085 128/200.16 |

FOREIGN PATENT DOCUMENTS

| | | | | |
|---|---|---|---|---|
| CN | 2461580 | Y | 11/2001 | |
| CN | 102716833 | A | * 10/2012 | B05B 17/06 |
| CN | 103736180 | A | 4/2014 | |
| CN | 203736645 | U | 7/2014 | |
| EP | 1190729 | A1 | 3/2002 | |

OTHER PUBLICATIONS

Aleem et al. "Piezoelectric and pyroelectric properties of Sr-doped PZT (PSZT) with minor manganese additions", 2013, Journal of Physics: Conference Series 439 012025.*

Dec. 29, 2014 International Search Report issued in International Patent Application No. PCT/CN2014/087366.

* cited by examiner

HANDHELD HIGH FREQUENCY ULTRASONIC NEBULIZER FOR WHOLE RESPIRATORY TRACT DRUG DELIVERY

FIELD OF THE INVENTION

The present disclosure pertains generally to devices and systems for drug delivery. More particularly, the present disclosure pertains to portable (handheld) devices and systems that use ultrasonic waves for nebulizing drug liquid to deliver to whole respiratory tracts.

BACKGROUND OF THE INVENTION

Drug delivery system for specific drugs has long been a field developed with medication. In order to be absorbed and utilized effectively, many liquid drugs must be converted through special methods into droplets (small particles) with specified sizes. The so-called ultrasonic nebulizer can convert liquid into small-diameter droplets, which through the resonance of the piezoelectric ceramic transducer leading to liquid conveying, and cavitations at some points on the surface of the liquid, through which droplets with certain range of diameter formed continually.

The existing ultrasonic nebulizers, limited by high voltages as required by piezoelectric transducers, usually get power from alternating currents using sockets or high voltage direct currents coming from a number of batteries. The higher power dissipation of the system will generate heats easily, which, on the one hand cause the system to be unstable, on the other hand, the activities of the drug molecules in the solution will probably be affected, the drugs become invalid due to denaturations or other transformations.

On the other hand, higher power dissipations require more accessories, and result in more large sizes of the devices, which means the device must be installed at specific location with alternating current power supply, or heavier devices cannot move easily. Moreover, higher power dissipations cause higher costs of the total atomizing system, limits the popularization and application in the majority of patients.

In addition, the existing ultrasonic nebulizers with a container existed within the specific site of the device usually is non-detachable, which makes against drugs' antiseptically storage, and to the disadvantage of the whole chamber's disinfection treatment, furthermore not convenient to clean up and greatly increases the chances of contaminations.

SUMMARY OF THE INVENTION

In accordance with the present disclosure, a handheld system and method are provided for nebulizing drug liquids into droplets wih micrometer-scale diameter through high frequency ultrasonic waves, which overcomes the shortcomings of existing techniques. In overview, the nebulizer includes a unique piezoelectric ceramic transducer made up of low power consumption materials, with small size, low costs and user-friendly setting. Accordingly, the nebulizer fits for whole respiratory tracts drug delivery treatment, which conveys most drug molecules into lower respiratory tracts, and then into the blood eventually to whole body.

The technical proposal envisioned for the present disclosure is as follows. A portable high frequency ultrasonic nebulizing device for whole respiratory tracts drug delivery includes a shell with open space, which includes an air inlet on the bottom and a lid on the upper mouth of the shell, while the lid includes a spray nozzle. There locates a drug solution cup with open mouth within the shell and a hood for spray collection on the cup, and the bottom of the hood is located in the mouth of the cup. The upper portion of the hood links tightly with the inner layer of the shell, and a gap is between the outer layer of the hood and the inner layer of the cup. The device (nebulizer) includes two chambers: the first one lies between the outer layer of the cup and the inner layer of the shell, the second one lies between the outer layer of the hood and the inner layer of the shell. A piezoelectric ceramic transducer locates at the upper portion of the cup and below the preset maximal liquid level. The cup layers link with the shell through some linkers, where some air vents existing around the linkers and/or layers of cup above the maximal liquid level to link the first chamber and the second chamber. Moreover, several spray outlets on the top of the hood connect with the spray nozzle through vertical air vent. There is a blowing device located near the air inlet for blasting air towards the spray nozzle. The drug delivery system can also include a circuit board to control the spray links with the piezoelectric ceramic transducer, which comprises piezoelectric main body, the upper electrode layer and the lower electrode layer covered upon the piezoelectric main body's upper and lower surfaces respectively, the upper electrode layer comprises a covered part upon the piezoelectric main body's upper surface, and an extended part extending from the covered part to the piezoelectric main body's lower surface through downward bending, which enclose the edges of the piezoelectric main body. The lower electrode layer covered upon the piezoelectric main body's lower surface, whose edges are kept at a proper distance to the extended part of the upper electrode layer. The upper electrode layer away from the piezoelectric main body's upper surface comprises a protective layer to protect the upper electrode. The piezoelectric main body is made up of low power consumption materials, whose major components include:

63.3-68.3% weight percentage lead tetraoxide ($Pb_3O_4$);
14.2-15.3% weight percentage zirconium dioxide ($ZrO_2$);
8.1-9.5% weight percentage titanium dioxide ($TiO_2$);
4.6-5.2% weight percentage strontium oxide (SrO);
1.5-1.8% weight percentage iron sesquioxide ($Fe_2O_3$);
1.0-1.4% weight percentage stannic oxide ($SnO_2$).

The piezoelectric main body further includes following additive components:

0.3-1.1% weight percentage manganese dioxide ($MnO_2$);
0.5-0.8% weight percentage cerium sesquioxide ($Ce_2O_3$);
0.4-0.8% weight percentage columbium pentoxide ($Nb_2O_5$);
0.3-0.7% weight percentage zinc oxide (ZnO);

In the application process, the total weight is designed according to weight percentage for all the components mentioned above. Additive components are prepared first, followed by the addition of main ingredients. With careful calculation, the components with lower weight percentage are added till the upper limit, whereas the components with higher weight percentage are added till the lower limit, in order to have the total weight in a reasonable ratio.

As indicated above, the piezoelectric ceramic transducer of the present disclosure is made of low power consuming materials, including the major components and additive components. The composition results in low voltage driver to generate high frequency ultrasound and produce relatively smaller size droplets with higher atomizing performances. The titanium dioxide from the major components improves the overall stability of ceramics, further extends the life span and achieves a much stabler quality. The four additive components with specific ratios significantly improve the capability of the ceramics with the piezoelectric constant d33 between 328 and 391 pC/N, the electromechanical coupling factor $k_p$ between 57.6% and 69.1%, the mechanical quality factor Om (Q-factor) between 1519 and 1654. Therefore, the piezoelectric ceramic is stimulated more easily to produce ultrasonic vibration.

Preferably, the surface of the piezoelectric main body is fixed up with multiple cavities.

More preferably, the cavities are circular, oval, square, rectangular, diamond, triangle cavities, and combinations thereof. The shapes of the cavities can be circular, oval, square, rectangular, diamond, triangle and other regular of irregular polygons, and theirs combinations thereof. The cavities of a piezoelectric ceramic transducer can contain one kind of dent shape or several kinds of various dent shapes. The quantity of cavities on the surface of a piezoelectric ceramic transducer is arbitrary, which will be dependent on the size of ceramic and application requirements, the density of the cavities distribution can be uniformly, can also be non-uniformly distribution. Additionally, the quantity of cavities on the surface of a piezoelectric ceramic with specific shape is any appropriate amount. The depths of cavities are arbitrary according to special processing method, which are depended upon the actual demands of the whole nebulizing system.

Preferably, there are several spray outlets evenly circumferential interval arranged along top of the hood. Therefore, the larger droplets will be detained in the chamber; however, the smaller droplets can be released freely through the spray outlets, and then can be spouted from the spray nozzle for user inhalation. The efficacy of the drug utilization efficiency is greatly improved. The spray outlets can be arranged non-uniformly according to the actual demands.

Preferably, the vertical section of piezoelectric transducer is extended along with a certain radian.

More preferably, the radian of the arc is between 0-π, means that the piezoelectric transducer has a curve shape with the radian from 0 to π. The shape of the aforementioned piezoelectric transducer is flat or bending (the whole shape is square of rectangular in the flat condition). The radian of the transducer, which is between 0-π, is dependent on the requirements of drug delivery. Meanwhile, the shape of transducer can be partially curved in some special embodiments. In these cases, the whole transducer body is preferably symmetric with the curved parts are distributed in both sides. The skilled technicians can adjust the shape of transducer according to actual demands, for example, some bends of the discontinuity are listed on the transducer with other parts are flat.

Furthermore, the ultrasonic frequency generated from the piezoelectric transducer is between 1.0-10 megahertz (MHz). As envisioned for the present disclosure, the piezoelectric materials of the transducer with lower power dissipation shows high frequency atomizing with high efficacy and small droplets. Most of the droplets can enter lower respiratory tract efficiently, achieving whole respiratory tract drug delivery.

More preferably, the ultrasonic frequency generated from the piezoelectric transducer is between 3.0-6.0 MHz.

Furthermore, the diameter of the droplets generated from the piezoelectric transducer is between 0.1-5 micrometer (μm), the median particle diameter is 2.5-3 μm.

More preferably, the diameter of the droplets generated from the piezoelectric transducer is between 2-4 micrometer (μm), the median particle diameter is 2.5-3 μm.

Preferably, the upper electrode layer and the lower electrode layer are made of gold or silver materials. The upper electrode layer is protected with alloy or enamel protective layer, which can protect the upper electrode layer from damages.

Preferably, the present portable high frequency ultrasonic nebulizer also includes a battery pack to supply power for the atomizing control circuit board and/or blowing installment.

More preferably, the voltage of the battery is between 1.5 v-10 v. More specifically, the voltage of the battery is between 1.5 v-4.5 v. The present disclosure provides a method to produce high frequency ultrasonic driving by low voltage with more small droplets and much lower power dissipation. The good performance of this method is due to the special piezoelectric ceramic materials, the curved shape of the transducer, and cavities on the surface.

Furthermore, the atomizing control circuit board of the present disclosure are equipped with liquid level detection function, the control circuit board will cut off the circuit when the level of drug solution in the drug cup decreased to a certain height or vacant, the whole system will shut down and shows warnings of liquid shortage.

Moreover, the atomizing control circuit board of the present disclosure doses drug quantitatively. The user can set spray specific volumes of drug delivery according to a required dosage.

The atomizing control circuit board modulates the voltage within a certain range of frequency and peak value. Moreover, the output frequency of the atomizing circuit board will match actively with the natural frequency of the piezoelectric ceramic transducer. The atomizing control circuit board will automatic adjust frequency and output peak voltage to bring resonance of the piezoelectric transducer.

Preferably, the control circuit board is located in the shell, where a connection port for supply power to the control circuit board and/or blowing installment. In other words, the nebulizer device for whole respiratory tract drug delivery in the present disclosure can be driven by its own battery pack or by external power, which makes the device convenient in clinic use.

Furthermore, a drugging hatch set is included upon the shell for connecting medicine bottle or filling drug solution and an open hatch located at the hood's wall correspond to the drugging hatch of the shell. The drugging hatch can be used to add drug solution, or connects with standard medicine bottle tightly through favorable interface. The interface can be screw type or slip-on style, or any other connective methods commonly used in the prior art.

More preferably, the handheld high frequency ultrasonic device nubilizer of the present disclosure also includes a mouthpiece or a breather mask linked to the spray nozzle, through which users can inhale drug conveniently.

In the present disclosure, when the atomizing control circuit board is provided power from battery pack or external DCs, the atomizing board will output electric signals with specific frequency within the range of working peak voltages of piezoelectric transducer, then piezoelectric transducer will produce well resonant oscillation that promotes the solution in the drug cup to generate high frequency resonance and atomizing upon the surface of the solution. An atomizing zone is formed inside the chamber. Meanwhile, the blowing device (for example, electric fans in some embodiments) driven by battery pack or external power impels the external air go into the nebulizing chamber through the air inlet continuously, which induces high pressure inside the chamber and them the droplets are spouted out from the spray outlets and the spray nozzle.

In accordance with the present disclosure, a handheld ultrasonic nebulizer and method are provided for atomizing constantly, the nebulizer can spray out a specific volume of mist uniformly in the given time. As long as volume of liquid is greater than the dead volume, the atomization can be achieved uniformly.

The handheld high frequency ultrasonic nebulizer for whole respiratory tract delivery can be used as atomization system for a variety of drugs, including drug aqueous solution, water-soluble drugs, organic solution accelerating drug delivery (for example, alcoholic solution of specific ratios) and suspension, to deliver drug locally and in system. Preferably, the nebulizer is used for drug solution or suspension atomization, especially for atomizing drugs/medicines to respiratory delivery, more preferably, primarily for the treatment of highly pathogenic influenza virus and related infectious diseases. Importantly, the atomizing drug in the aqueous solution can be small interfering RNAs, small chemical drugs, protein drugs, antibody drugs, refined Chinese medicines, and other drugs.

The handheld high frequency ultrasonic nebulizing device for whole respiratory tract delivery for the present disclosure generates resonance oscillation by piezoelectric ceramic transducer, which breaks the solution containing drugs into very small liquid particles (droplets). Further, the device is low power consumption, hand-held and portable; the small atomized droplets can reach the lower respiratory tract/pulmonary alveoli and further achieve whole respiratory diseases treatment. The piezoelectric ceramic transducer and its subsidiary items, drug cups and nebulizing chamber for the present disclosure are all detachable, which can be cleaned and disinfected for the easy to use.

Compared with the current technologies, the present disclosure shows the following advantages. The present disclosure provides a handheld high frequency ultrasonic nebulizing device for whole respiratory tract delivery. The transducer is made up of special ceramic materials of low power consumption, through which the overall size of the device is greatly reduced. It provides a portable/handheld device to whole respiratory tract drug delivery. Furthermore, the manufacturing cost of the device is significantly reduced, with great advantages and broad application futures.

As indicated above, with the present disclosure, the size of the droplets generated from the low power consumption high-frequency ultrasonic nebulizer is much smaller than any of available nebulizers on the market. This makes the nebulizer more easily delivery drug into lower respiratory tract/pulmonary alveoli. In contrast, the current available nebulizers produced much larger particles and can only deliver drugs to the upper respiratory tract. In addition, with the arrangement of drugging hatch and drug cup settings, drugs can be placed in the cup or connecting external medicine bottles. The drugs in the bottles can be easily replaced and is conveniently disinfecting the drug sprayer. The present disclosure of nubilizer uses high frequency ultrasound techniques, which takes full advantage of the unique materials of piezoelectric ceramic transducer and curved structures with cavities on the surface of the transducer. It effectively reduces system power consumption, and keeps the whole system operated under 2.5 W power, 1.5-10V, or even with 3-4.5V conditions. The device can continuously generate liquid drug solution to achieve efficient atomization, with the diameter of particle (droplets) much smaller than the conventional ultrasonic nebulizer. This is speciall convenient for lower respiratory tract drug delivery. The delivery device of the present disclosure, by controlling the atomized aqueous solution or suspend drug particle size distribution, enables a specific proportion of the drugs delivered into the lower respiratory tract/pulmonary alveoli, middle respiratory tract and upper respiratory tract, therefore to achieve the drug/medication delivery into the whole respiratory tract.

wherein: 1—shell; 2—air inlet; 3—spray nozzle; 4—drug solution cup; 5—piezoelectric ceramic transducer; 6—blowing device; 7—circuit board; 8—battery; 9—hood for spray collection; 10—drugging hatch; 11—spray outlet; 12—air gallery; 13—piezoelectric main body; 14—upper electrode layer; 15—lower electrode layer; 16—protective layer of the upper electrode; 17—mouthpiece; 18—breather mask; 19—the first chamber; 20—the second chamber.

DESCRIPTION OF THE PREFERRED EMBODIMENTS

Hereinafter, the detailed information is elucidated combined with the preferred embodiments, so that it is much more easily to be understood by skilled technicians in the field upon the advantages and features for the present disclosure, and further clarify the boundaries of the claimed rights of the present disclosure.

Figure 1:
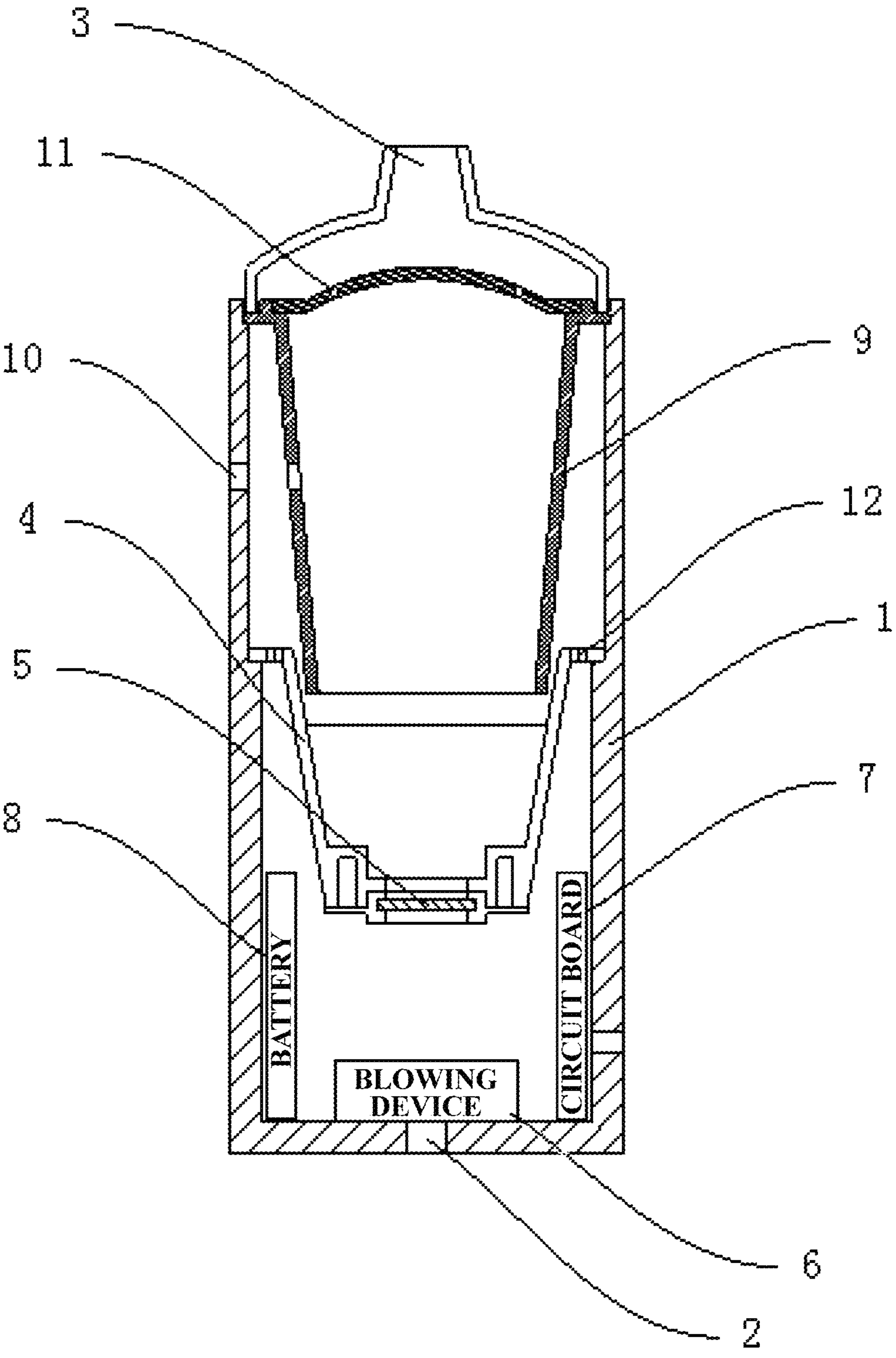
FIG. 1: Local section diagram of the handheld high frequency ultrasonic atomizing device for the present disclosure.

This invention provides a portable/handheld high frequency ultrasonic nebulizer for whole respiratory tract drug delivery. FIG. 1 showed a preferred embodiment of whole respiratory tract drug delivery device in accordance with the present disclosure. The device (nebulizer) includes a shell 1 with an air inlet 2 at the bottom and a lid on the top of the mouth of the shell 1 with the open space, and a spray nozzle 3 on the lid (shell 1 and lid are two separated components for conveniently disassembly. They can also designed as a whole). The device (nebulizer) further includes a drug solution cup 4 with open mouth within the shell 1 and a hood 9 for mist collection upon the cup 4, and the bottom of the hood is located in the mouth of the cup 4 and further a gap between the outer layer of the hood 9 and the inner layer of the cup 4 formed, and the upper portion (or middle portion in some embodiments) of the hood 9 links tightly with the inner layer of the shell 1. Between the outer layer of the cup 4 and the inner layer of the shell 1 is the first chamber 19, the second chamber 20 lies between the outer layer of the hood 9 and the inner layer of the shell 1. A piezoelectric ceramic transducer 5 locates at the upper portion of the cup 4 and below the preset maximal liquid level. The cup layers 4 connects with the shell 1 through some linkers, where some air vents 12 existing around the linkers and/or layers of cup 4 above the maximal liquid level to link the first chamber 19 and the second chamber 20. Moreover, several spray outlets 11 on the top of the hood 9 connect with the spray nozzle 3 through vertical air vent. The device can also include a blowing device 6 located near the air inlet 2 for blasting air towards the spray nozzle 3, and can further include a circuit board 7 to control the spray link with the piezoelectric ceramic transducer 5. The piezoelectric main body 13 is made up of low power consumption materials, include the following major components (mass percent): lead tetraoxide ($Pb_3O_4$, 63.3-68.3%), zirconium dioxide ($ZrO_2$, 14.2-15.3%), titanium dioxide ($TiO_2$, 8.1-9.5%), strontium oxide (SrO, 4.6-5.2%), iron sesquioxide ($Fe_2O_3$, 1.5-1.8%), stannic oxide ($SnO_2$, 1.0-1.4%), and the following additive components (mass percent): manganese dioxide ($MnO_2$, 0.3-1.1%), cerium sesquioxide ($Ce_2O_3$, 0.5-0.8%), columbium pentoxide ($Nb_2O_5$, 0.4-0.8%), zinc oxide (ZnO, 0.3-0.7%).

In the present preferred embodiment for the present disclosure, a piezoelectric ceramic transducer 5 locates at the bottom of the cup 4 and beneath the maximal drug solution level, which promotes to high performance of the atomizing. The cup 4 will resonate along with the piezoelectric ceramic transducer 5, which producing ultrasonic wavelength and atomizing the solution in the cup 4 into droplets. It will be appreciated, however, that the piezoelectric ceramic transducer 5 can be set at the side wall of the cup 4 or other locations, which will not limited by the present embodiment, which is just as an example.

In this embodiment, the wall of the cup 4 connects with the shell 1 through linkers, where air vents 12 around the linkers to link the first chamber 19 and the second chamber 20. Through the vents 12, the two chambers are connected and the airflow generated by the blowing device goes through from the first chamber 19 to the second chamber 20. Further the airflow is driven from the gap between the bottom out wall of the hood 9 and inside wall of the cup 4 into the hood 9, so that the drug droplets arising from the liquid level in the drug cup 4 flow upward inside the hood 9 and finally discharged through the spray outlet 11. Since all the detailed settings are easily understood by a technician in the art, any settings with similar functions with the vents should be under the protection scope of the present disclosure. For example, some vents can be located at the wall of the cup 4 and accordingly, in this case the vents should be higher than the maximal top liquid level to gain the airflow directly. Or the combination of these two vents can be used in an embodiment. The upper portion of the hood 9 and the shell 1 connect tightly, the top of where distributes spray outlets 11 (The headpiece of the hood 9 can be a natural part of the hood 9, or any other separate covers with spray outlets) connects with the spray nozzle 3 through vertical air vent. More specifically, the number of spray outlets 11 is not limited and distributed circumferentially with specific intervals, which blocks the bigger droplets and let the smaller droplets out of the spray nozzle 3 freely.

The present disclosure further includes an atomizing control circuit board 7 connecting with the piezoelectric ceramic transducer 5, and a battery pack 8 supplying power for the circuit board and/or blowing device. The piezoelectric ceramic transducer 5 comprises piezoelectric main body 13 whose surface is arranged with cavities, the upper electrode layer 14 and the lower electrode layer 15. The upper electrode layer 14 comprises a covered part upon the piezoelectric main body 13's upper surface, and an extended part extending from the covered part to the piezoelectric main body 13's lower surface through downward bending to enclose the edges of the piezoelectric main body 13. The lower electrode layer 15 covers upon the piezoelectric main body 13's lower surface, whose edges are kept from a proper distance to the extended part of the upper electrode layer 14. The upper electrode layer 14 away from the piezoelectric main body 13's upper surface comprises a protective layer 16 to protect the upper electrode. The piezoelectric main body 13 is made up of lower power dissipation materials. As can be envisioned for the present disclosure, the drug solution in the cup 4 is driven by high frequency resonance to form an atomizing zone, whose space is connected with the cavity inside of the hood 9, so the atomizing droplets will flow from the hood 9, the spray outlets 11 upon the hood 9 to the spray nozzle 3 and then conveniently used by patients. In this embodiment, the blowing device is a fan, the first chamber 19 and the second chamber 20 lies respectively between the outer layer of the cup 4 and the inner layer of the shell 1, and between the outer layer of the hood 9 and the inner layer of the shell 1, which forms a channel for fluid circulation. The fan 6 provides airflow to the inner space of the device through the air inlet 2, and then the airflow will flow to the spray nozzle 3 through the first chamber 19 between the cup 4 and the inner layer of the shell 1, further through the vents 12 located on the linkers around drug cup 4 and shell 1 go into the second chamber 20 between the outer layer of the hood 9 and the inner layer of the shell 1. Additionally, the upper portion of the hood 9 connects tightly with the shell 1, the lower portion is located in the open of drug cup 4, where the a gap exists between the outer layer of the hood 9 and the inner layer of the shell 1, so that the airflow from the air gap can be blown into the lower inner space of the hood 9 with upward flow, and further the droplets in the drug cup 4 will be driven upwardly. Furthermore, the droplets are expelled through the spray outlet 11 on the top of the hood 9 and the spray nozzle 3 on the lid, and then delivered into the respiratory tracts and pulmonary alveoli through mouthpiece 17 connecting with the spray nozzle 3 or through breather mask 18. That is, an airflow channel is formed from the air inlet 2, the vents 12, the first chamber 19, the second chamber 20, and the spray outlet 11 to the spray nozzle 3, through which the airflow promoting resonance generated from the piezoelectric ceramic transducer 5, pushing the atomized droplets expelled through the spray nozzle 3 into the patients/users.

The materials of the piezoelectric main body for the present disclosure include the following major components:

63.3% weight percentage lead tetraoxide ($Pb_3O_4$);
14.7% weight percentage zirconium dioxide ($ZrO_2$);
8.7% weight percentage titanium dioxide ($TiO_2$);
4.9% weight percentage strontium oxide (SrO);
1.7% weight percentage iron sesquioxide ($Fe_2O_3$);
1.2% weight percentage stannic oxide ($SnO_2$);
and following additive components:
0.7% weight percentage manganese dioxide ($MnO_2$);
0.6% weight percentage cerium sesquioxide ($Ce_2O_3$);
0.7% weight percentage columbium pentoxide ($Nb_2O_5$);
0.5% weight percentage zinc oxide (ZnO).

In the present embodiment, the upper electrode layer 14 and the lower electrode layer 15 of the piezoelectric ceramic transducer 5 are gold electrode layers, and the protective layer 16 of the upper electrode is ceramic protection layer. The device further includes a drugging hatch 10 set upon the shell 1 for connecting medicine bottle or filling drug solution, and an open hatch located at the hood 9's wall corresponding to the drugging hatch 10 of the shell 1. The drugging hatch 10 and the aforementioned open hatch are used for installing the external medicine bottle or filling drug solution into the drug cup 4.

Figure 2:
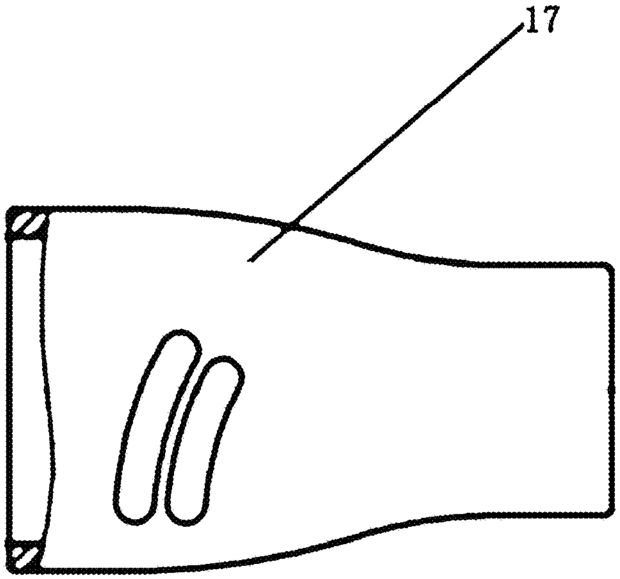
FIG. 2: Sketch view of the mouthpiece for the present disclosure.
Figure 3:
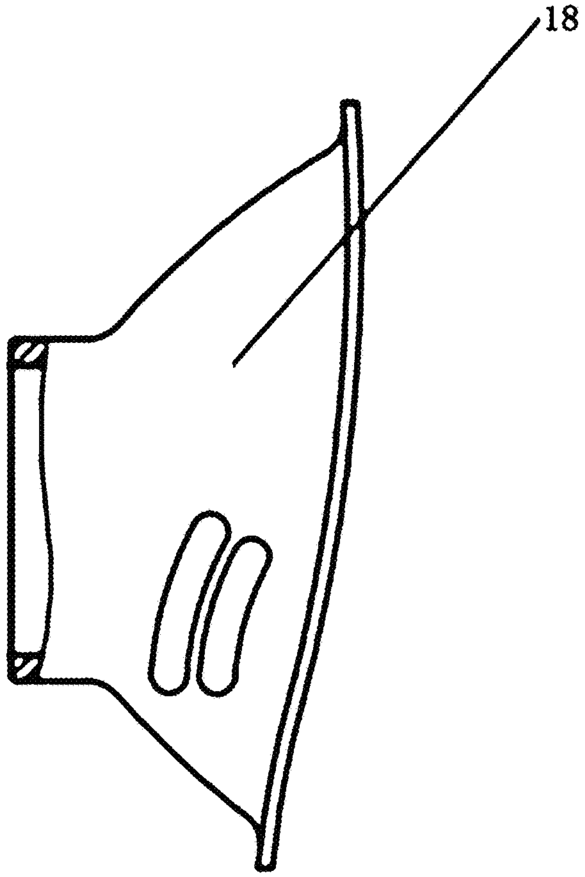
FIG. 3: Sketch view of breather mask for the present disclosure.

The device of the present embodiment further includes a battery pack 8 with the voltage between 1.5 v-4.5 v to supply power to the circuit board 7 and/or the blowing device 6. The circuit board 7 drives the piezoelectric ceramic transducer 5 by the battery pack 8, or through connection port to gain external voltages. In any cases, only 1.5-10 v, preferably 1.5-4.5 v of the power is needed. Namely, by using the curved surface structural designing transducer of the present application made up of low power consumption, only several volts generated from ordinary battery is sufficient to drive the transducer. The atomizing control circuit board 7 is arranged inside the shell 1, where a connection port is installed to supply power to the circuit board 7 and/or the blowing device 6. As shown in FIG. 2 and FIG. 3, the device also includes a mouthpiece 17 or a breather mask 18 linked to the spray nozzle 3 through some linkers, whose size and shape are exactly well matched with the spray nozzle 3. The linker can directly snap into and connect tightly with the spray nozzle 3 by forces of friction contact surface, which impels the whole atomizing droplets with appropriate sizes ejecting uniformly through the mouthpiece 17 or the breather mask 18.

Figure 4:
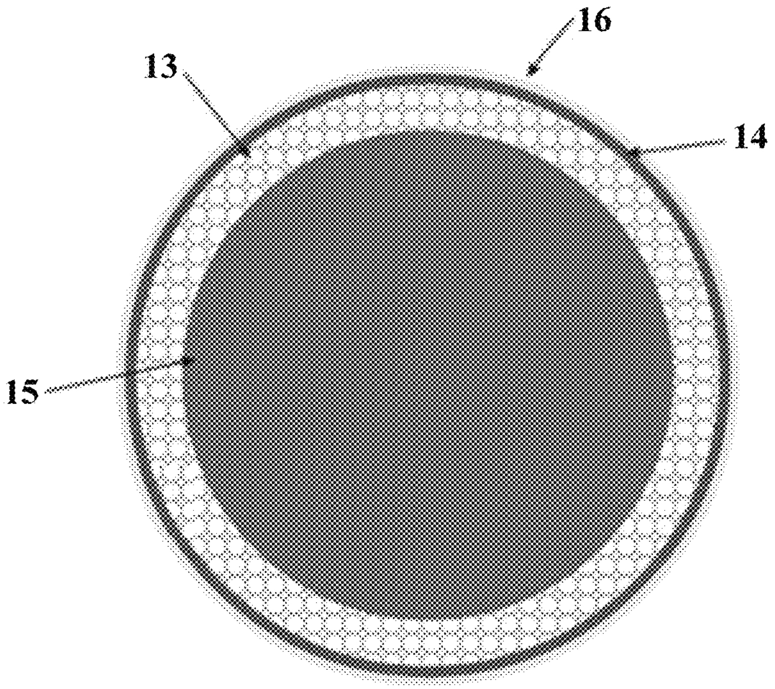
FIG. 4: Upward view of piezoelectric ceramic transducer for the present disclosure.

A whole set of cavities is distributed on the surface of the piezoelectric main body 13 with the shape of circular, oval, square, rectangular, diamond, triangle or theirs combinations. The longitudinal section of the piezoelectric ceramic transducer 5 is arc-shaped in the main. FIG. 4 shows the upward view of the piezoelectric ceramic transducer 5, and FIG. 5 is the downward view of the piezoelectric ceramic transducer 5, and FIG. 6 shows the longitudinal section diagram of the piezoelectric ceramic transducer 5.

Figure 5:
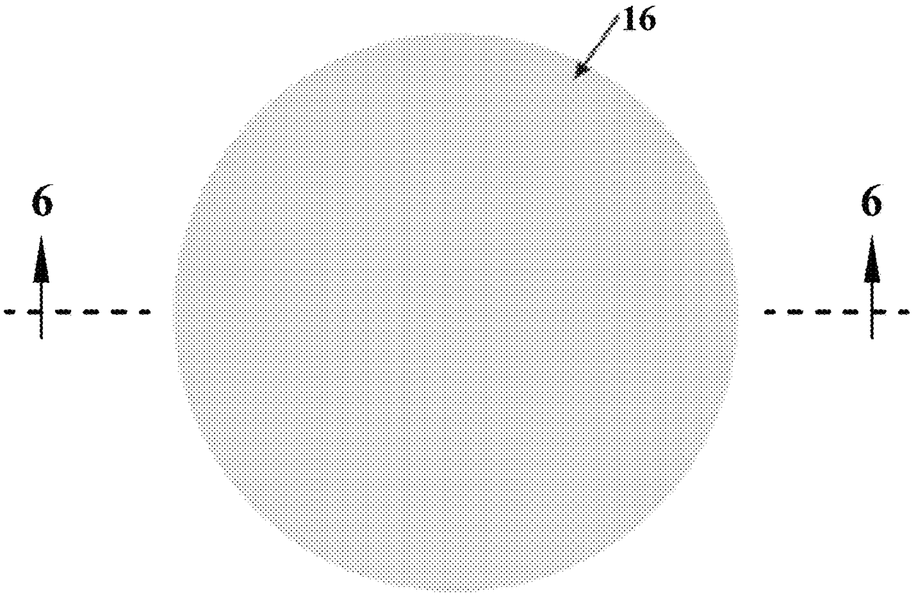
FIG. 5: Downward view of piezoelectric ceramic transducer for the present disclosure.
Figure 6:
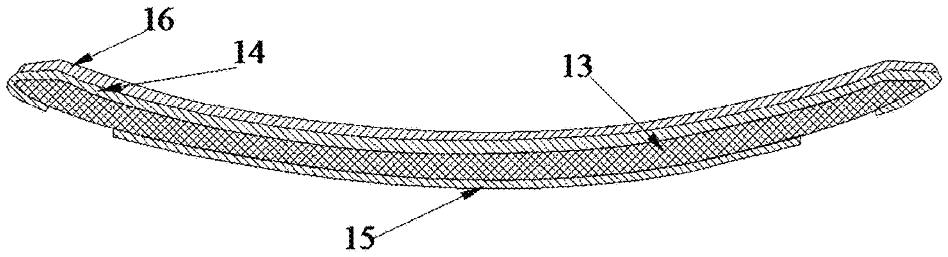
FIG. 6: Section view of piezoelectric ceramic transducer for the present disclosure.

Referring now to FIG. 5, the shape of the piezoelectric ceramic transducer 5 in this embodiment is circular curved surface structure, or partially circular curved or even discontinuous multiple circular curved structures. The radian of the arc is an arbitrary value between 0-π. For example, the radian value of the transducer is π/4, equivalent to the circular arc corresponding to a 45° radius angle. In another example, both ends of the transducer are of planar structures, while the middle is a semi-circle curved structure.

As shown in the figures, the piezoelectric ceramic transducer 5 for the present disclosure includes piezoelectric main body 13 as the major component, whose surface is arranged with some cavities with specific sizes and shapes. The shape, quantity, density and depth of these cavities include but not limited to the following conditions: all the cavities with any specific quantity (such as 100 or 200) on a transducer surface are circular; A part of cavities (appropriate quantity) on a transducer surface are circular, other cavities (appropriate quantity) are square; A part of cavities (appropriate quantity) on a transducer surface are oval, some (appropriate quantity) are diamond, the rest others (appropriate quantity) are irregular polygons. Further, the density distribution of the cavities on a transducer can be uniformly, or can be non-uniformly distributed with some areas are more dense than other areas. Additionally, the density of cavities on the surface of a piezoelectric ceramic transducer can be an appropriate value, which is dependent on the preparation process and application requirements.

Figure 7:
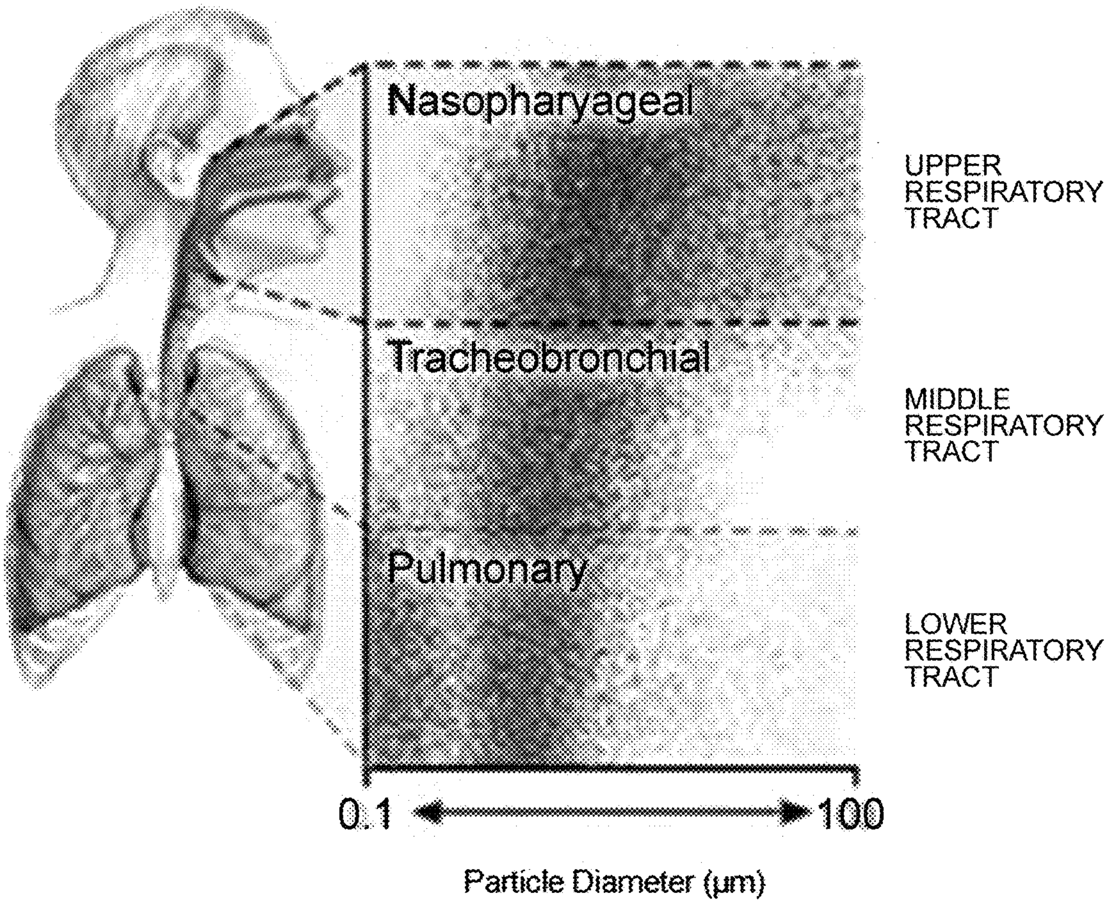
FIG. 7: Sketch view of distribution of different sizes atomized droplets in the respiratory tract after drug delivery.

The present disclosure is a high frequency ultrasonic nebulizing device for whole respiratory tract drug delivery with low power consumption. It is characterized with much smaller droplets generation through high frequency ultrasound. The main body of the diameter of the droplets generated in the present device falls in the scope of 2-4 micrometer (μm) which can be delivered into the lower respiratory tract/pulmonary alveoli; whereas a small part of relatively bigger droplets will be distributed into the upper and middle respiratory tracts. During inhaled drug delivery, the distribution position of the droplets in the tracts is highly dependent on the sizes of the droplets, as shown in FIG. 7. The bigger of the droplets is, the more possibility it distributed in upper respiratory tract. When the size of the droplets decreased, it will be distributed into the lower respiratory tract/pulmonary alveoli.

The droplets generated by the drug delivery device of the present disclosure are relatively smaller than droplets generated from similar products, and mainly enter into the lower respiratory tract via inhalation. FIG. 8 showed the diameter of the droplets measured by laser diffraction (LD) particle sizing technique by Spraytec Laser Diffraction System from Malvern Instruments (Spraytec, Malvern, UK), which shows the difference of the of droplets in size between the present invested nebulizer and a nebulizer made of Omron (refer to D50 distribution). The median diameter of the droplets generated by the present invented handheld high frequency ultrasonic nebulizer for whole respiratory tract drug delivery is 5.13 micrometer (μm) (FIG. 8A), while the median diameter of the droplets generating by Omron nebulizer is 10.14 micrometer (μm) (FIG. 8B). Alternatively, when the diameter of the droplets is measured by Aerodynamic Particle Sizer Spectrometer (Model APS-3321) using time-of-flight method, and the sizes of the droplets are compared between the present invented nebulizer and a nebulizer made of Omron (refer to mean mass distribution). The median diameter of the droplets generated by the present invented high frequency handheld ultrasonic nebulizer for whole respiratory tract drug delivery is 1.43 micrometer (μm) (FIG. 9A), while the median diameter of the droplets generating by Omron nebulizer is 2.63 micrometer (μm) (FIG. 9B). The results from the two detection methods show that the droplets generated by present invented handheld high frequency ultrasonic nebulizer for whole respiratory tract drug delivery are about 50% smaller than the droplets generating by Omron nebulizer.

Therefore, this handheld high frequency ultrasonic device for whole respiratory tract drug delivery has the advantages of low power consumption, portable and low manufacturing costs, as well as much smaller atomizing droplets generated. All of the characters makes the present invented device (nebulizer) very suitable for efficiently delivering drugs into the whole respiratory tract, with broader applications in the futures.

Hereinbefore, the present invented particular nebulizer, system and method as herein shown and disclosed in detail is fully capable of obtaining the objects and providing the advantages herein before stated, it is to be understood that it is merely illustrative of the presently preferred embodiments of the invention, many other possible modifications and variations can be made without departing from the spirit and scope of the invention claimed.

The invention claimed is:

1. A handheld high frequency ultrasonic atomizing device for delivering drugs to a person's whole respiratory tract, which comprises:
- a shell with open space, which includes an air inlet on the bottom;
- a lid on an upper mouth of the shell;
- a spray nozzle on the lid;
- a drug solution cup with an open mouth and a hood above the cup located within the shell, a bottom of the hood being located within the open mouth of the cup, an upper portion of the hood linking tightly with an inner surface of the shell, with a gap between an outer surface of the hood and an inner surface of the cup, the device including a first chamber lying between the outer surface of the cup and the inner surface of the shell and a second chamber lying between the outer surface of the hood and the inner surface of the shell;
- a piezoelectric ceramic transducer located in the cup and below a preset maximal liquid level, the cup linking with the shell through a linker;
- a plurality of air vents for connecting the first chamber and the second chamber, the plurality of air vents being provided on the linker and/or an upper part of the cup which is above the preset maximal liquid level;
- several spray outlets being provided on a top of the hood and connected with the spray nozzle;
- a blowing device located near the air inlet for blasting air towards the spray nozzle; and
- a circuit board connecting with the piezoelectric ceramic transducer, wherein:
- the piezoelectric ceramic transducer comprises a piezoelectric main body, an upper electrode layer and a lower electrode layer covered upon the piezoelectric main body;
- the upper electrode layer comprises a covered part upon an upper surface of the piezoelectric main body, and a curved part extending downward from the covered part to a lower surface of the piezoelectric main body to enclose edges of the piezoelectric main body;
- the lower electrode layer covered upon the lower surface of the piezoelectric main body, with an edge kept at a distance to the curved part of the upper electrode layer;
- the upper electrode layer is covered by a protective layer;
- the piezoelectric main body is made up of low power dissipation materials, whose major components include:
  - 63.3-68.3% weight percentage lead tetraoxide;
  - 14.2-15.3% weight percentage zirconium dioxide;
  - 8.1-9.5% weight percentage titanium dioxide;
  - 4.6-5.2% weight percentage strontium oxide;
  - 1.5-1.8% weight percentage iron sesquioxide; and
  - 1.0-1.4% weight percentage stannic oxide; and
- the piezoelectric main body further includes following additive components:
  - 0.3-1.1% weight percentage manganese dioxide;
  - 0.5-0.8% weight percentage cerium sesquioxide;
  - 0.4-0.8% weight percentage columbium pentoxide; and
  - 0.3-0.7% weight percentage zinc oxide.

2. The handheld high frequency ultrasonic atomizing device as recited in claim 1, wherein:
- a plurality of cavities are set on the upper surface and the lower surface of the piezoelectric main body, whose shapes include but not limited to circular, oval, square, rectangle, prismatic, triangle and their combinations.

3. The handheld high frequency ultrasonic atomizing device as recited in claim 1, wherein
- said several spray outlets are evenly arranged along a circumferential direction.

4. The handheld high frequency ultrasonic atomizing device as recited in claim 1, wherein
- a longitudinal section of the piezoelectric ceramic transducer is shaped as an arc, which travels through an angle between 0 to $\pi$ radians.

5. The handheld high frequency ultrasonic atomizing device as recited in claim 1, wherein
- a plurality of ultrasonic frequencies of the piezoelectric ceramic transducer are between 1.0 to 10 mega hertz.

6. The handheld high frequency ultrasonic atomizing device as recited in claim 1, wherein
- diameters of atomized drug particles formed by the piezoelectric ceramic transducer are between 0.1 to 5 micrometers.

7. The handheld high frequency ultrasonic atomizing device as recited in claim 1, wherein:
- the upper electrode layer and the lower electrode layer of the piezoelectric ceramic transducer are a gold electrode or a silver electrode, and
- the protective layer is an alloy coating or a ceramic protection layer.

8. The handheld high frequency ultrasonic atomizing device as recited in claim 1, further comprising a battery to supply power to the circuit board and/or the blowing device.

9. The handheld high frequency ultrasonic atomizing device as recited in claim 1, wherein a voltage of the battery is between 1.5 to 10 Volts.

10. The handheld high frequency ultrasonic atomizing device as recited in claim 1, wherein:
- the circuit board is placed inside the shell, with a port of wiring on the shell for the circuit board and/or the blowing device connect with a power.

11. The handheld high frequency ultrasonic atomizing device as recited in claim h wherein:
- a drugging hatch is set upon the shell for connecting with a medicine bottle or filling a drug solution, and
- an open hatch located at the spray hood's wall corresponds to the drugging hatch of the shell.

12. The handheld high frequency ultrasonic atomizing device as recited in claim 1, further comprising a mouthpiece or a breather mask linked to the spray nozzle.

* * * * *

UNITED STATES PATENT AND TRADEMARK OFFICE
CERTIFICATE OF CORRECTION

PATENT NO. : 10,195,368 B2
APPLICATION NO. : 14/891890
DATED : February 5, 2019
INVENTOR(S) : Wang et al.

It is certified that error appears in the above-identified patent and that said Letters Patent is hereby corrected as shown below:

Please delete Pat. No. 10,195,368 B2 in its entirety and insert Pat. No. 10,195,368 B2 in its entirety as shown on the attached pages.

Signed and Sealed this
Sixteenth Day of April, 2019

Andrei Iancu
*Director of the United States Patent and Trademark Office*

(12) United States Patent
Wang et al.

(10) Patent No.: US 10,195,368 B2
(45) Date of Patent: Feb. 5, 2019

(54) HANDHELD HIGH FREQUENCY ULTRASONIC NEBULIZER FOR WHOLE RESPIRATORY TRACT DRUG DELIVERY

(71) Applicants: CHANGZHOU ZHENGYUAN MEDICAL TECHNOLOGY CO., LTD., Changzhou, Jiangsu (CN); GUANGZHOU NANOTIDES PHARMACEUTICALS CO., LTD., Guangzhou, Guangdong (CN)

(72) Inventors: Cheng Wang, Changzhou (CN); Patrick Y. Lu, Guangzhou (CN); Chuntian Lu, Guangzhou (CN); Songlin Jiang, Changzhou (CN); Shenggao Tang, Guangzhou (CN); Tao Yuan, Changzhou (CN)

(73) Assignees: CHANGZHOU ZHENGYUAN MEDICAL TECHNOLOGY CO., LTD., Changzhou (CN); GUANGZHOU NANOTIDES PHARMACEUTICALS CO., LTD., Guangzhou (CN)

( * ) Notice: Subject to any disclaimer, the term of this patent is extended or adjusted under 35 U.S.C. 154(b) by 563 days.

(21) Appl. No.: 14/891,890

(22) PCT Filed: Sep. 25, 2014

(86) PCT No.: PCT/CN2014/087366
§ 371 (c)(1),
(2) Date: Nov. 17, 2015

(87) PCT Pub. No.: WO2015/103891
PCT Pub. Date: Jul. 16, 2015

(65) Prior Publication Data

US 2016/0279352 A1 Sep. 29, 2016

(30) Foreign Application Priority Data

Jan. 13, 2014 (CN) .......................... 2014 1 0013105

(51) Int. Cl.
*A61M 11/00* (2006.01)
*A61M 15/00* (2006.01)
(Continued)

(52) U.S. Cl.
CPC ......... *A61M 11/005* (2013.01); *A61M 11/003* (2014.02); *A61M 15/0085* (2013.01);
(Continued)

(58) Field of Classification Search
CPC ................ A61M 11/00; A61M 11/005; A61M 15/0085; A61M 15/0086; A61M 15/008;
(Continued)

(56) References Cited

U.S. PATENT DOCUMENTS 4,976,259 A * 12/1990 Higson ................ A61M 11/005 128/200.14
5,908,158 A * 6/1999 Cheiman ............ B05B 17/0615 128/200.16
(Continued)

FOREIGN PATENT DOCUMENTS

CN 2137964 Y 7/1993
CN 2232326 Y * 8/1996 .............. B06B 1/06
(Continued)

OTHER PUBLICATIONS

Omron MicroAir Handheld Ultrasonic Portable Nebulizer, retrieved from the WayBack Machine: http://www.allergyasthmatech.com/P/Omron_MicroAir_Handheld_Ultrasonic_Portable_Nebulizer/733 Available on: Mar. 7, 2012.*
(Continued)

*Primary Examiner* — Scott Medway
*Assistant Examiner* — Jacqueline Pinderski
(74) *Attorney, Agent, or Firm* — Oliff PLC

(57) ABSTRACT

A handheld high frequency ultrasonic atomizing device for delivering drugs to whole respiratory tract comprising a shell with an air inlet and a lid with a spray nozzle. A drug cup with a piezoelectric transducer and a hood with a spray outlet are provided within the shell. The components of piezoelectric ceramic transducer are as follows (mass percentage): lead tetraoxide 63.3-68.3%, zirconium dioxide 14.2-15.3%, titanium dioxide 8.1-9.5%, strontium oxide 4.6-5.2%, iron sesquioxide 1.5-1.8%, stannic oxide 1.0-1.4%, manganese dioxide 0.3-1.1%, cerium sesquioxide 0.5-0.8%, columbium pentoxide 0.4-0.8% and zinc oxide 0.3-0.7%. This device is small in size, with low power consumption and lower cost, and is able to produce mist
(Continued)

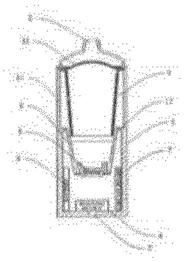

with small particle size. The device can efficiently deliver drug liquid into the whole respiratory tract, especially down to the lower respiratory tract and pulmonary alveoli through carrying drug molecules in mist particles.

12 Claims, 8 Drawing Sheets

(51) Int. Cl.
*A61M 16/06* (2006.01)
*A61M 16/00* (2006.01)

(52) U.S. Cl.
CPC ..... *A61M 15/0021* (2014.02); *A61M 16/0066* (2013.01); *A61M 16/06* (2013.01); *A61M 2205/3386* (2013.01); *A61M 2205/8206* (2013.01)

(58) Field of Classification Search
CPC ......... B05B 17/00; B05B 17/04; B05B 17/06; B05B 17/0607; B05B 17/0638; B05B 17/0646; B05B 17/0661
See application file for complete search history.

(56) References Cited

U.S. PATENT DOCUMENTS 6,283,118 B1 * 9/2001 Lu ........................ A61M 11/005 128/200.16
2007/0295328 A1 12/2007 Raghuprasad
2008/0245362 A1 * 10/2008 Moessis ............ A61M 15/0085 128/200.16
2010/0083956 A1 * 4/2010 Fukumoto ......... A61M 15/0085 128/200.14
2014/0083174 A1 * 3/2014 Reboud ................ H01J 49/165 73/61.59
2014/0216443 A1 * 8/2014 Hu .................... A61M 15/0085 128/200.16

FOREIGN PATENT DOCUMENTS

CN 2461580 Y 11/2001
CN 102716833 A * 10/2012 ............. B05B 17/06
CN 103736180 A 4/2014
CN 203736645 U 7/2014
EP 1190729 A1 3/2002

OTHER PUBLICATIONS

Aleem et al. "Piezoelectric and pyroelectric properties of Sr-doped PZT (PSZT) with minor manganese additions", 2013, Journal of Physics: Conference Series 439 012025.*
Dec. 29, 2014 International Search Report issued in International Patent Application No. PCT/CN2014/087366.

* cited by examiner

HANDHELD HIGH FREQUENCY ULTRASONIC NEBULIZER FOR WHOLE RESPIRATORY TRACT DRUG DELIVERY

FIELD OF THE INVENTION

The present disclosure pertains generally to devices and systems for drug delivery. More particularly, the present disclosure pertains to portable (handheld) devices and systems that use ultrasonic waves for nebulizing drug liquid to deliver to whole respiratory tracts.

BACKGROUND OF THE INVENTION

Drug delivery system for specific drugs has long been a field developed with medication. In order to be absorbed and utilized effectively, many liquid drugs must be converted through special methods into droplets (small particles) with specified sizes. The so-called ultrasonic nebulizer can convert liquid into small-diameter droplets, which through the resonance of the piezoelectric ceramic transducer leading to liquid conveying, and cavitations at some points on the surface of the liquid, through which droplets with certain range of diameter formed continually.

The existing ultrasonic nebulizers, limited by high voltages as required by piezoelectric transducers, usually get power from alternating currents using sockets or high voltage direct currents coming from a number of batteries. The higher power dissipation of the system will generate heats easily, which, on the one hand cause the system to be unstable, on the other hand, the activities of the drug molecules in the solution will probably be affected, the drugs become invalid due to denaturations or other transformations.

On the other hand, higher power dissipations require more accessories, and result in more large sizes of the devices, which means the device must be installed at specific location with alternating current power supply, or heavier devices cannot move easily. Moreover, higher power dissipations cause higher costs of the total atomizing system, limits the popularization and application in the majority of patients.

In addition, the existing ultrasonic nebulizers with a container existed within the specific site of the device usually is non-detachable, which makes against drugs' antiseptically storage, and to the disadvantage of the whole chamber's disinfection treatment, furthermore not convenient to clean up and greatly increases the chances of contaminations.

SUMMARY OF THE INVENTION

In accordance with the present disclosure, a handheld system and method are provided for nebulizing drug liquids into droplets wih micrometer-scale diameter through high frequency ultrasonic waves, which overcomes the shortcomings of existing techniques. In overview, the nebulizer includes a unique piezoelectric ceramic transducer made up of low power consumption materials, with small size, low costs and user-friendly setting. Accordingly, the nebulizer fits for whole respiratory tracts drug delivery treatment, which conveys most drug molecules into lower respiratory tracts, and then into the blood eventually to whole body.

The technical proposal envisioned for the present disclosure is as follows. A portable high frequency ultrasonic nebulizing device for whole respiratory tracts drug delivery includes a shell with open space, which includes an air inlet on the bottom and a lid on the upper mouth of the shell, while the lid includes a spray nozzle. There locates a drug solution cup with open mouth within the shell and a hood for spray collection on the cup, and the bottom of the hood is located in the mouth of the cup. The upper portion of the hood links tightly with the inner layer of the shell, and a gap is between the outer layer of the hood and the inner layer of the cup. The device (nebulizer) includes two chambers: the first one lies between the outer layer of the cup and the inner layer of the shell, the second one lies between the outer layer of the hood and the inner layer of the shell. A piezoelectric ceramic transducer locates at the upper portion of the cup and below the preset maximal liquid level. The cup layers link with the shell through some linkers, where some air vents existing around the linkers and/or layers of cup above the maximal liquid level to link the first chamber and the second chamber. Moreover, several spray outlets on the top of the hood connect with the spray nozzle through vertical air vent. There is a blowing device located near the air inlet for blasting air towards the spray nozzle. The drug delivery system can also include a circuit board to control the spray links with the piezoelectric ceramic transducer, which comprises piezoelectric main body, the upper electrode layer and the lower electrode layer covered upon the piezoelectric main body's upper and lower surfaces respectively, the upper electrode layer comprises a covered part upon the piezoelectric main body's upper surface, and an extended part extending from the covered part to the piezoelectric main body's lower surface through downward bending, which enclose the edges of the piezoelectric main body. The lower electrode layer covered upon the piezoelectric main body's lower surface, whose edges are kept at a proper distance to the extended part of the upper electrode layer. The upper electrode layer away from the piezoelectric main body's upper surface comprises a protective layer to protect the upper electrode. The piezoelectric main body is made up of low power consumption materials, whose major components include:

63.3-68.3% weight percentage lead tetraoxide ($Pb_3O_4$);
14.2-15.3% weight percentage zirconium dioxide ($ZrO_2$);
8.1-9.5% weight percentage titanium dioxide ($TiO_2$);
4.6-5.2% weight percentage strontium oxide (SrO);
1.5-1.8% weight percentage iron sesquioxide ($Fe_2O_3$);
1.0-1.4% weight percentage stannic oxide ($SnO_2$).

The piezoelectric main body further includes following additive components:

0.3-1.1% weight percentage manganese dioxide ($MnO_2$);
0.5-0.8% weight percentage cerium sesquioxide ($Ce_2O_3$);
0.4-0.8% weight percentage columbium pentoxide ($Nb_2O_5$);
0.3-0.7% weight percentage zinc oxide (ZnO);

In the application process, the total weight is designed according to weight percentage for all the components mentioned above. Additive components are prepared first, followed by the addition of main ingredients. With careful calculation, the components with lower weight percentage are added till the upper limit, whereas the components with higher weight percentage are added till the lower limit, in order to have the total weight in a reasonable ratio.

As indicated above, the piezoelectric ceramic transducer of the present disclosure is made of low power consuming materials, including the major components and additive components. The composition results in low voltage driver to generate high frequency ultrasound and produce relatively smaller size droplets with higher atomizing performances. The titanium dioxide from the major components improves the overall stability of ceramics, further extends the life span and achieves a much stabler quality. The four additive components with specific ratios significantly improve the capability of the ceramics with the piezoelectric constant d33 between 328 and 391 pC/N, the electromechanical coupling factor $k_p$ between 57.6% and 69.1%, the mechanical quality factor Om (Q-factor) between 1519 and 1654. Therefore, the piezoelectric ceramic is stimulated more easily to produce ultrasonic vibration.

Preferably, the surface of the piezoelectric main body is fixed up with multiple cavities.

More preferably, the cavities are circular, oval, square, rectangular, diamond, triangle cavities, and combinations thereof. The shapes of the cavities can be circular, oval, square, rectangular, diamond, triangle and other regular of irregular polygons, and theirs combinations thereof. The cavities of a piezoelectric ceramic transducer can contain one kind of dent shape or several kinds of various dent shapes. The quantity of cavities on the surface of a piezoelectric ceramic transducer is arbitrary, which will be dependent on the size of ceramic and application requirements, the density of the cavities distribution can be uniformly, can also be non-uniformly distribution. Additionally, the quantity of cavities on the surface of a piezoelectric ceramic with specific shape is any appropriate amount. The depths of cavities are arbitrary according to special processing method, which are depended upon the actual demands of the whole nebulizing system.

Preferably, there are several spray outlets evenly circumferential interval arranged along top of the hood. Therefore, the larger droplets will be detained in the chamber; however, the smaller droplets can be released freely through the spray outlets, and then can be spouted from the spray nozzle for user inhalation. The efficacy of the drug utilization efficiency is greatly improved. The spray outlets can be arranged non-uniformly according to the actual demands.

Preferably, the vertical section of piezoelectric transducer is extended along with a certain radian.

More preferably, the radian of the arc is between 0-π, means that the piezoelectric transducer has a curve shape with the radian from 0 to π. The shape of the aforementioned piezoelectric transducer is flat or bending (the whole shape is square of rectangular in the flat condition). The radian of the transducer, which is between 0-π, is dependent on the requirements of drug delivery. Meanwhile, the shape of transducer can be partially curved in some special embodiments. In these cases, the whole transducer body is preferably symmetric with the curved parts are distributed in both sides. The skilled technicians can adjust the shape of transducer according to actual demands, for example, some bends of the discontinuity are listed on the transducer with other parts are flat.

Furthermore, the ultrasonic frequency generated from the piezoelectric transducer is between 1.0-10 megahertz (MHz). As envisioned for the present disclosure, the piezoelectric materials of the transducer with lower power dissipation shows high frequency atomizing with high efficacy and small droplets. Most of the droplets can enter lower respiratory tract efficiently, achieving whole respiratory tract drug delivery.

More preferably, the ultrasonic frequency generated from the piezoelectric transducer is between 3.0-6.0 MHz.

Furthermore, the diameter of the droplets generated from the piezoelectric transducer is between 0.1-5 micrometer (μm), the median particle diameter is 2.5-3 μm.

More preferably, the diameter of the droplets generated from the piezoelectric transducer is between 2-4 micrometer (μm), the median particle diameter is 2.5-3 μm.

Preferably, the upper electrode layer and the lower electrode layer are made of gold or silver materials. The upper electrode layer is protected with alloy or enamel protective layer, which can protect the upper electrode layer from damages.

Preferably, the present portable high frequency ultrasonic nebulizer also includes a battery pack to supply power for the atomizing control circuit board and/or blowing installment.

More preferably, the voltage of the battery is between 1.5 v-10 v. More specifically, the voltage of the battery is between 1.5 v-4.5 v. The present disclosure provides a method to produce high frequency ultrasonic driving by low voltage with more small droplets and much lower power dissipation. The good performance of this method is due to the special piezoelectric ceramic materials, the curved shape of the transducer, and cavities on the surface.

Furthermore, the atomizing control circuit board of the present disclosure are equipped with liquid level detection function, the control circuit board will cut off the circuit when the level of drug solution in the drug cup decreased to a certain height or vacant, the whole system will shut down and shows warnings of liquid shortage.

Moreover, the atomizing control circuit board of the present disclosure doses drug quantitatively. The user can set spray specific volumes of drug delivery according to a required dosage.

The atomizing control circuit board modulates the voltage within a certain range of frequency and peak value. Moreover, the output frequency of the atomizing circuit board will match actively with the natural frequency of the piezoelectric ceramic transducer. The atomizing control circuit board will automatic adjust frequency and output peak voltage to bring resonance of the piezoelectric transducer.

Preferably, the control circuit board is located in the shell, where a connection port for supply power to the control circuit board and/or blowing installment. In other words, the nebulizer device for whole respiratory tract drug delivery in the present disclosure can be driven by its own battery pack or by external power, which makes the device convenient in clinic use.

Furthermore, a drugging hatch set is included upon the shell for connecting medicine bottle or filling drug solution and an open hatch located at the hood's wall correspond to the drugging hatch of the shell. The drugging hatch can be used to add drug solution, or connects with standard medicine bottle tightly through favorable interface. The interface can be screw type or slip-on style, or any other connective methods commonly used in the prior art.

More preferably, the handheld high frequency ultrasonic device nubilizer of the present disclosure also includes a mouthpiece or a breather mask linked to the spray nozzle, through which users can inhale drug conveniently.

In the present disclosure, when the atomizing control circuit board is provided power from battery pack or external DCs, the atomizing board will output electric signals with specific frequency within the range of working peak voltages of piezoelectric transducer, then piezoelectric transducer will produce well resonant oscillation that promotes the solution in the drug cup to generate high frequency resonance and atomizing upon the surface of the solution. An atomizing zone is formed inside the chamber. Meanwhile, the blowing device (for example, electric fans in some embodiments) driven by battery pack or external power impels the external air go into the nebulizing chamber through the air inlet continuously, which induces high pressure inside the chamber and them the droplets are spouted out from the spray outlets and the spray nozzle.

In accordance with the present disclosure, a handheld ultrasonic nebulizer and method are provided for atomizing constantly, the nebulizer can spray out a specific volume of mist uniformly in the given time. As long as volume of liquid is greater than the dead volume, the atomization can be achieved uniformly.

The handheld high frequency ultrasonic nebulizer for whole respiratory tract delivery can be used as atomization system for a variety of drugs, including drug aqueous solution, water-soluble drugs, organic solution accelerating drug delivery (for example, alcoholic solution of specific ratios) and suspension, to deliver drug locally and in system. Preferably, the nebulizer is used for drug solution or suspension atomization, especially for atomizing drugs/medicines to respiratory delivery, more preferably, primarily for the treatment of highly pathogenic influenza virus and related infectious diseases. Importantly, the atomizing drug in the aqueous solution can be small interfering RNAs, small chemical drugs, protein drugs, antibody drugs, refined Chinese medicines, and other drugs.

The handheld high frequency ultrasonic nebulizing device for whole respiratory tract delivery for the present disclosure generates resonance oscillation by piezoelectric ceramic transducer, which breaks the solution containing drugs into very small liquid particles (droplets). Further, the device is low power consumption, hand-held and portable; the small atomized droplets can reach the lower respiratory tract/pulmonary alveoli and further achieve whole respiratory diseases treatment. The piezoelectric ceramic transducer and its subsidiary items, drug cups and nebulizing chamber for the present disclosure are all detachable, which can be cleaned and disinfected for the easy to use.

Compared with the current technologies, the present disclosure shows the following advantages. The present disclosure provides a handheld high frequency ultrasonic nebulizing device for whole respiratory tract delivery. The transducer is made up of special ceramic materials of low power consumption, through which the overall size of the device is greatly reduced. It provides a portable/handheld device to whole respiratory tract drug delivery. Furthermore, the manufacturing cost of the device is significantly reduced, with great advantages and broad application futures.

As indicated above, with the present disclosure, the size of the droplets generated from the low power consumption high-frequency ultrasonic nebulizer is much smaller than any of available nebulizers on the market. This makes the nebulizer more easily delivery drug into lower respiratory tract/pulmonary alveoli. In contrast, the current available nebulizers produced much larger particles and can only deliver drugs to the upper respiratory tract. In addition, with the arrangement of drugging hatch and drug cup settings, drugs can be placed in the cup or connecting external medicine bottles. The drugs in the bottles can be easily replaced and is conveniently disinfecting the drug sprayer. The present disclosure of nubilizer uses high frequency ultrasound techniques, which takes full advantage of the unique materials of piezoelectric ceramic transducer and curved structures with cavities on the surface of the transducer. It effectively reduces system power consumption, and keeps the whole system operated under 2.5 W power, 1.5-10V, or even with 3-4.5V conditions. The device can continuously generate liquid drug solution to achieve efficient atomization, with the diameter of particle (droplets) much smaller than the conventional ultrasonic nebulizer. This is speciall convenient for lower respiratory tract drug delivery. The delivery device of the present disclosure, by controlling the atomized aqueous solution or suspend drug particle size distribution, enables a specific proportion of the drugs delivered into the lower respiratory tract/pulmonary alveoli, middle respiratory tract and upper respiratory tract, therefore to achieve the drug/medication delivery into the whole respiratory tract.

BRIEF DESCRIPTION OF THE DRAWINGS

Figure 8A:
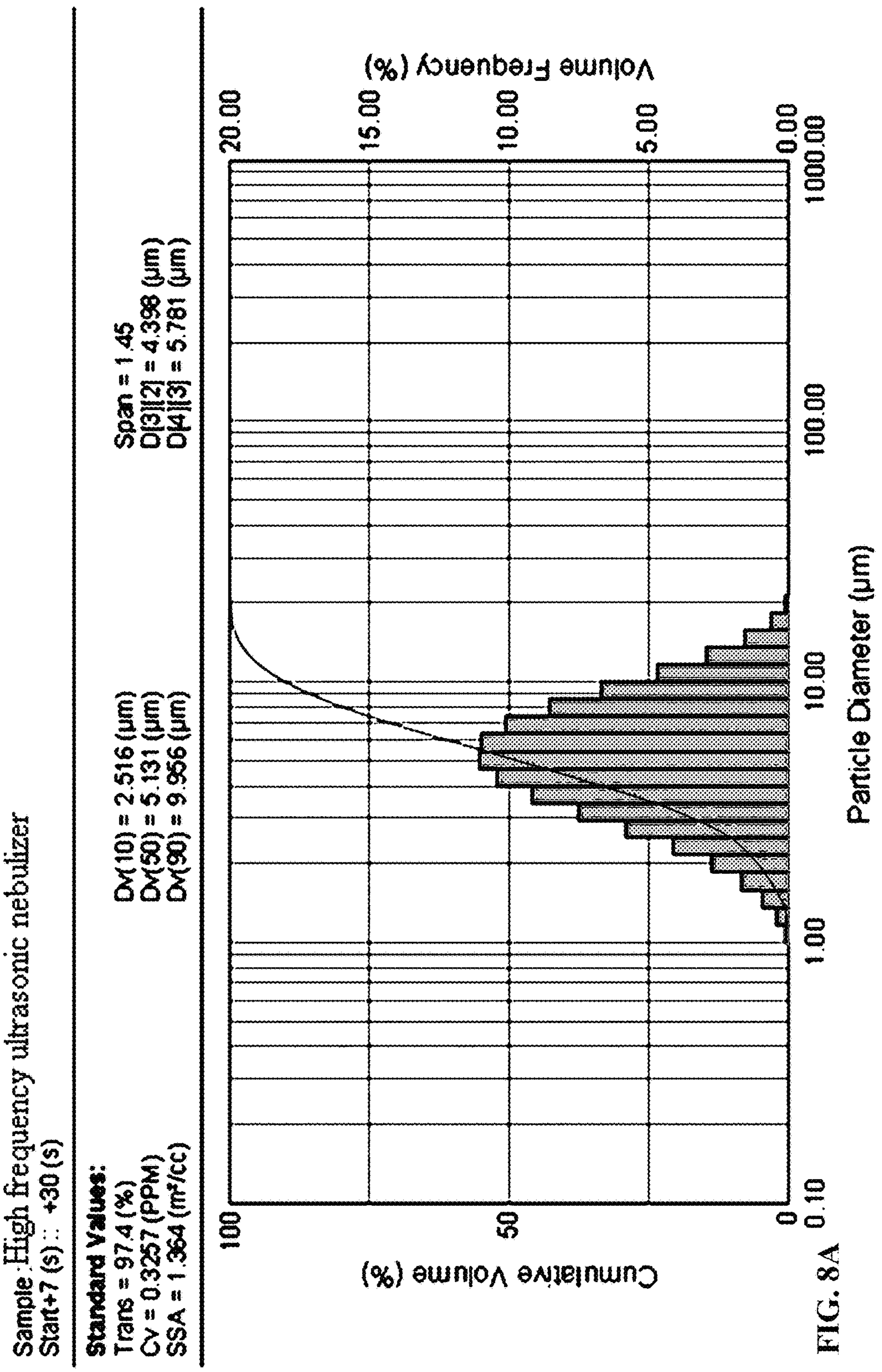
FIGS. 8A and 8B: The atomizing effects diagram of the comparison between the drug delivery device for the present disclosure and current nebulizer device available in market by laser diffraction (LD) method.
Figure 8B:
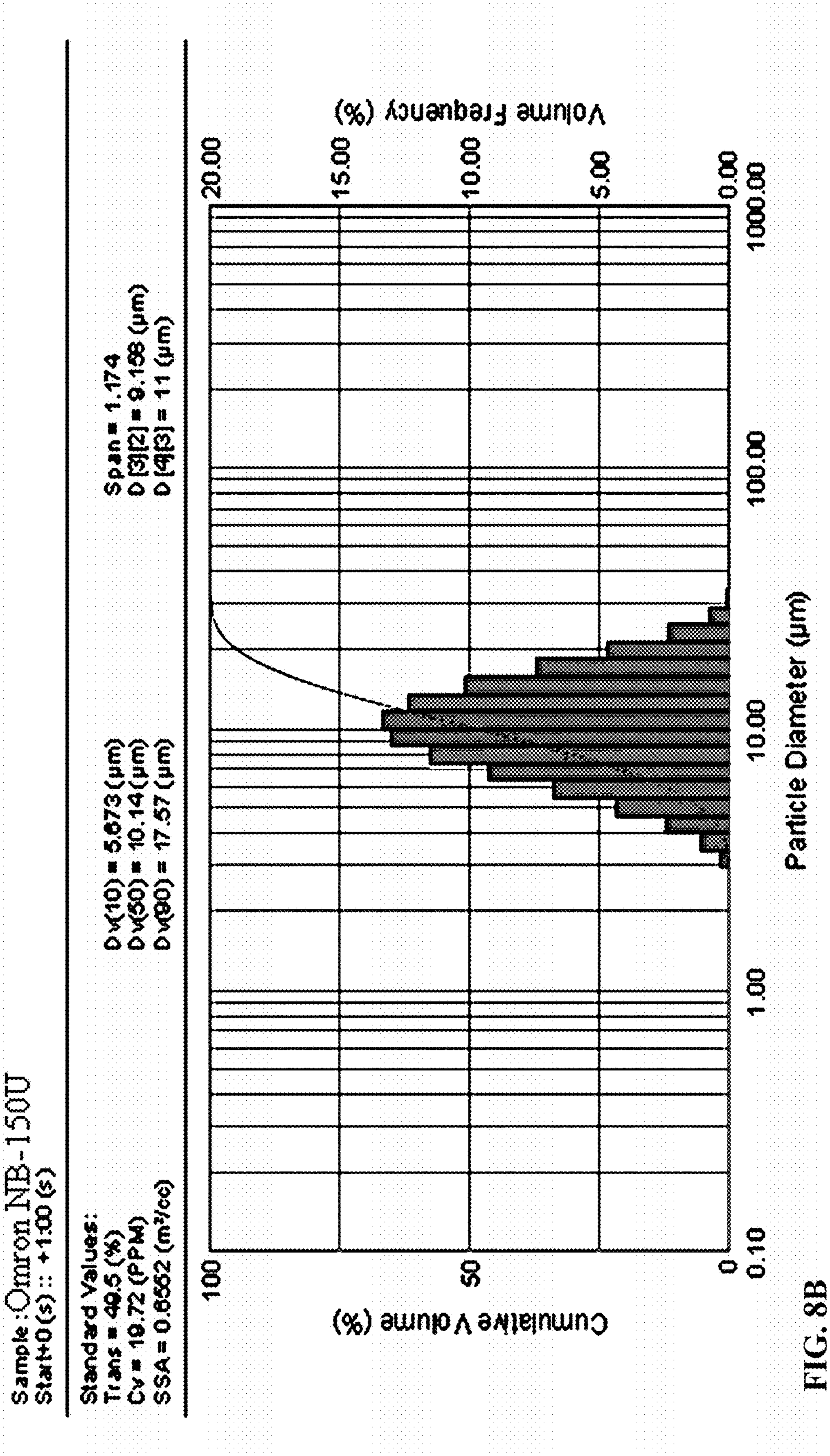
Figure 9A:
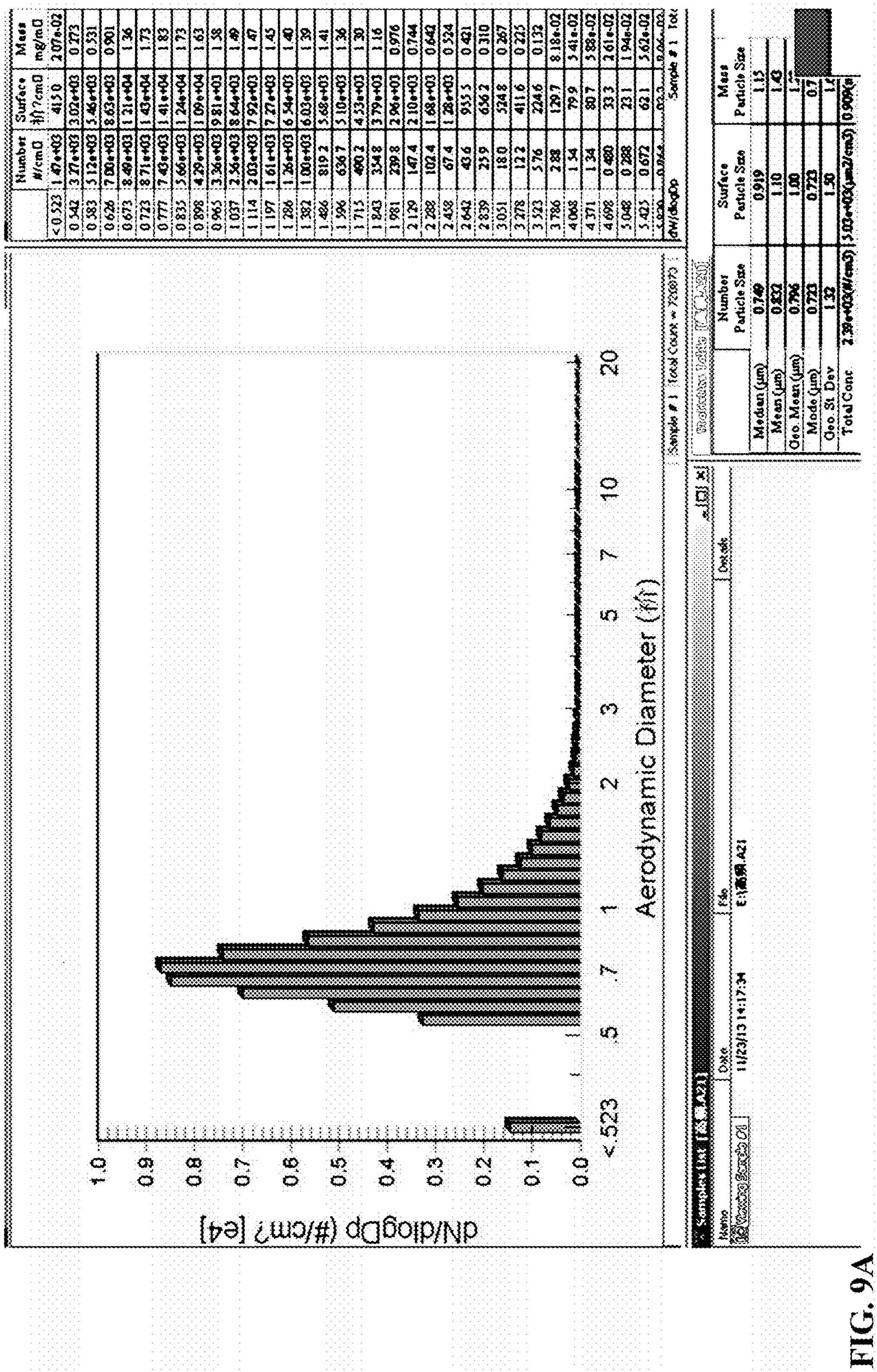
FIGS. 9A and 9B: The atomizing effects diagram of the comparison between the drug delivery device for the present disclosure and current nebulizer device available in market by time-of-flight (TOF) aerodynamic particle size analysis.
Figure 9B:
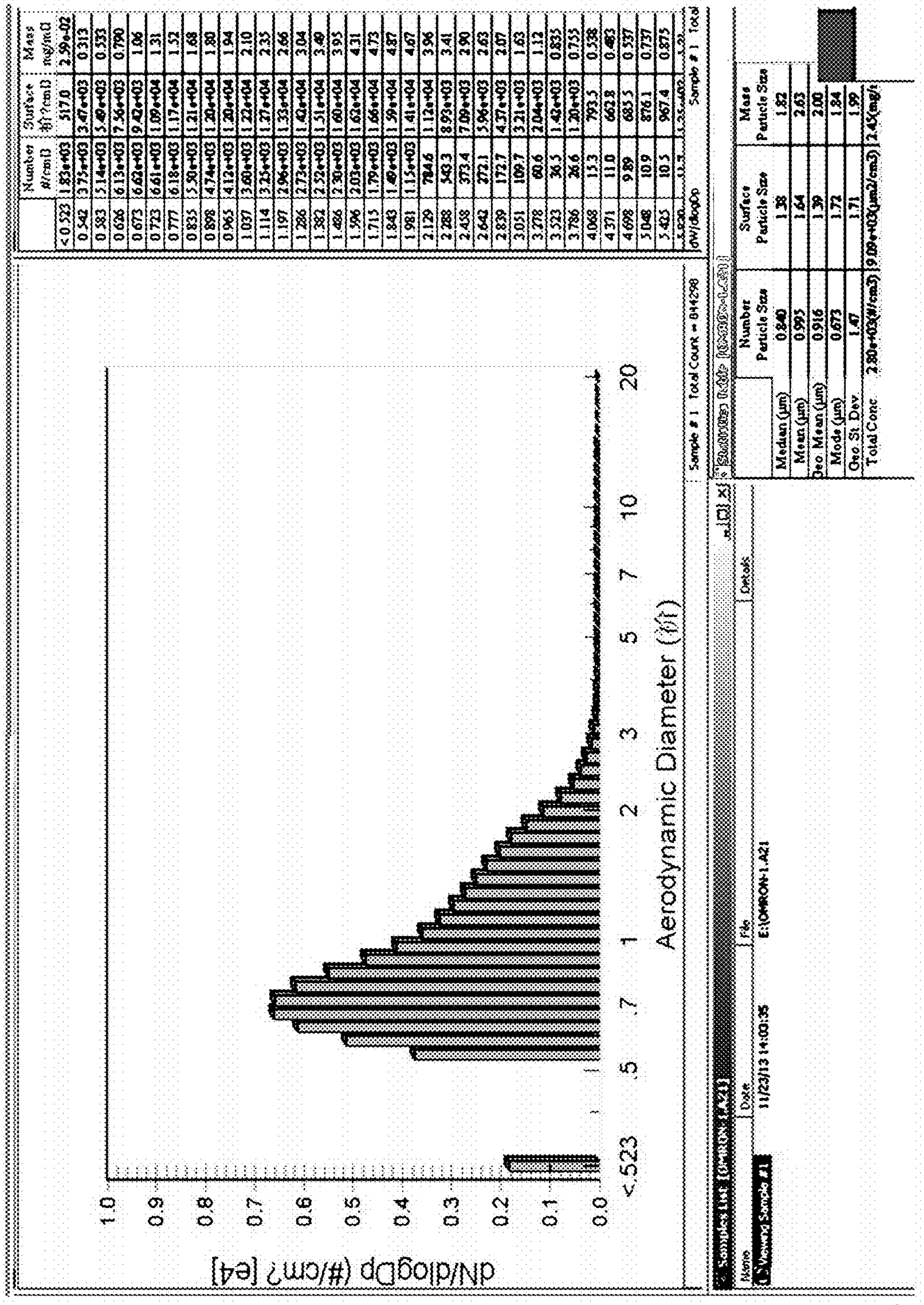
Figure 1:
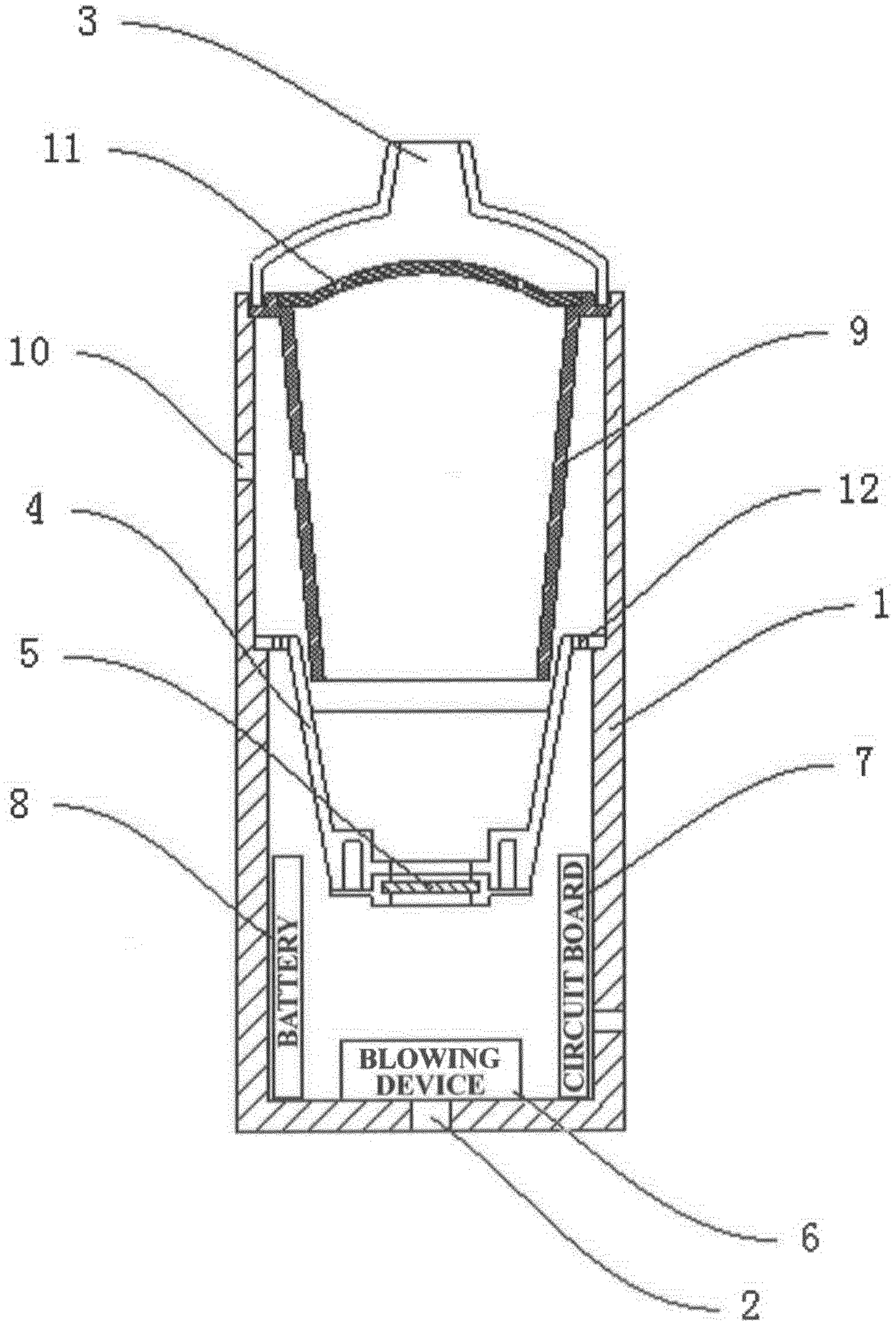
Figure 2:
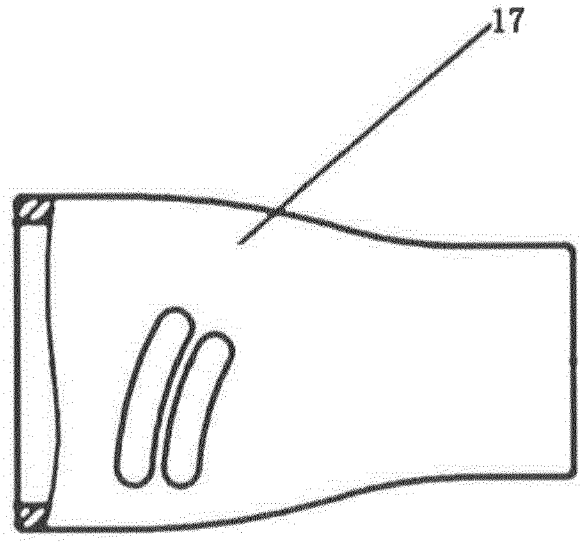
Figure 3:
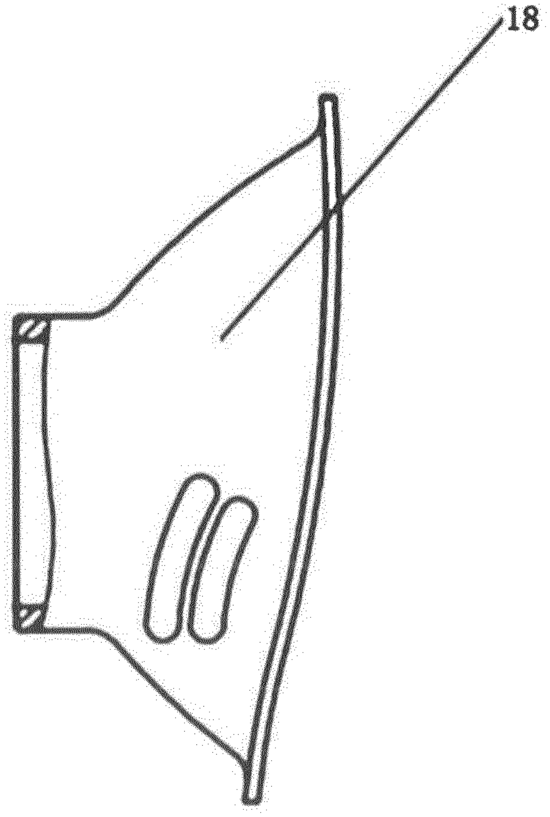
Figure 4:
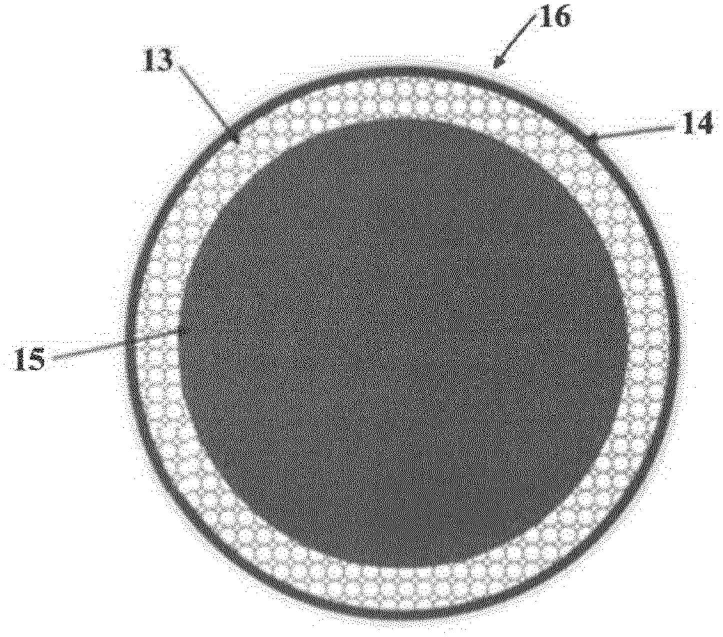
Figure 5:
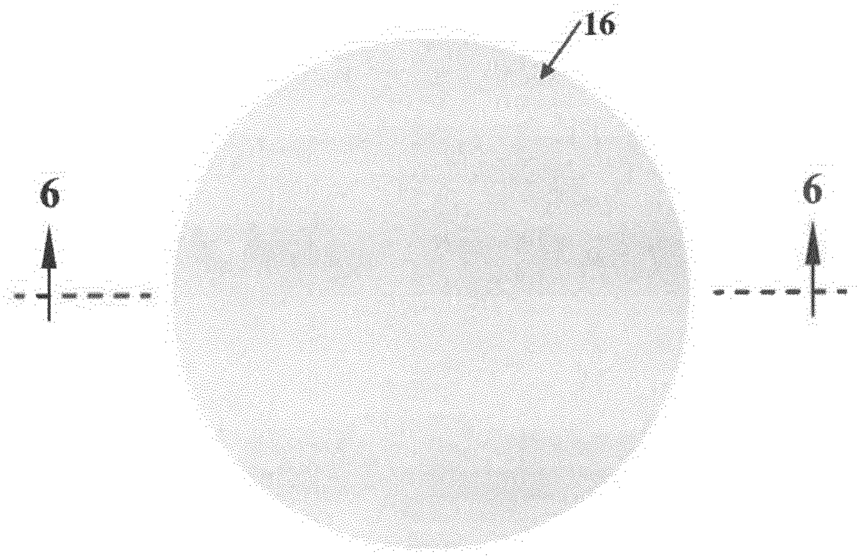
Figure 6:
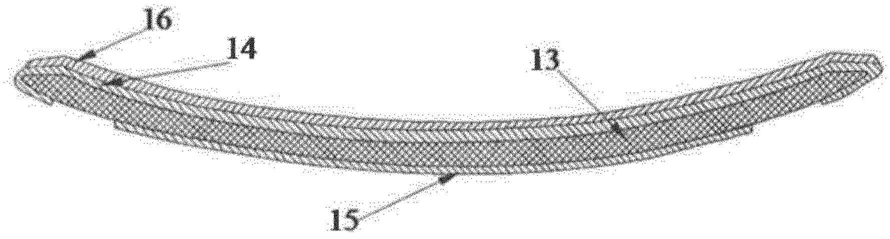
Figure 7:
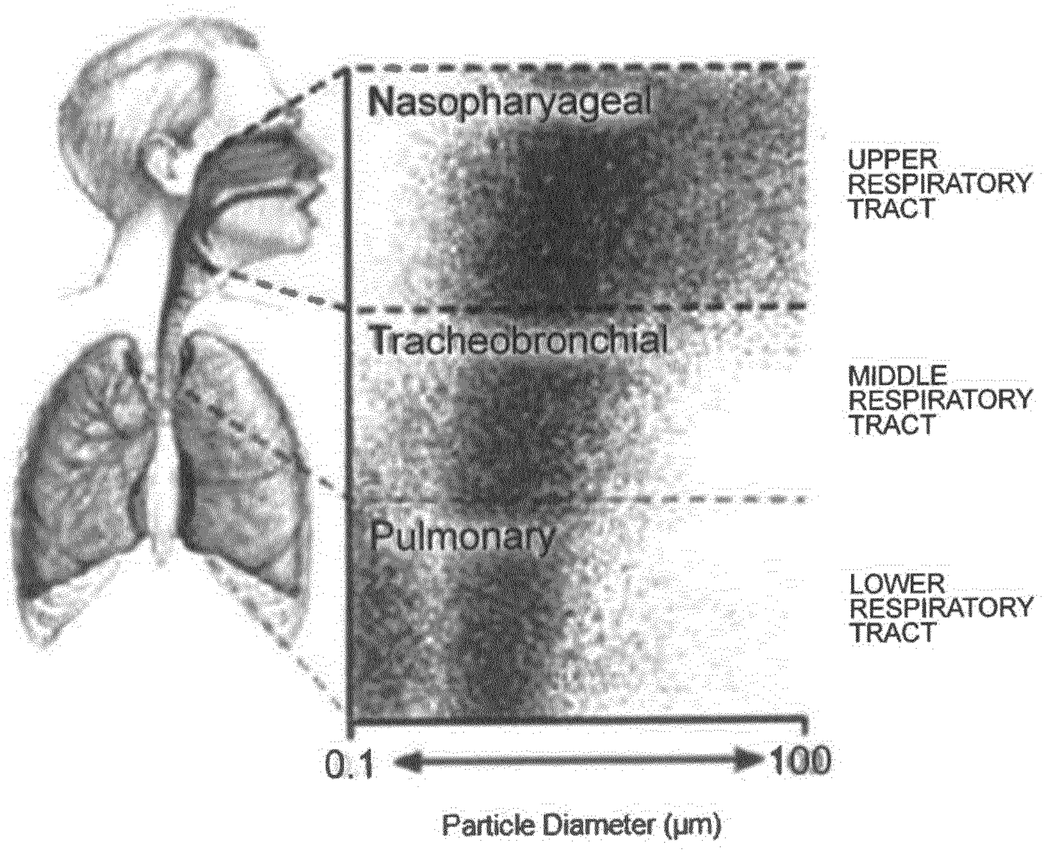
Figure 8A:
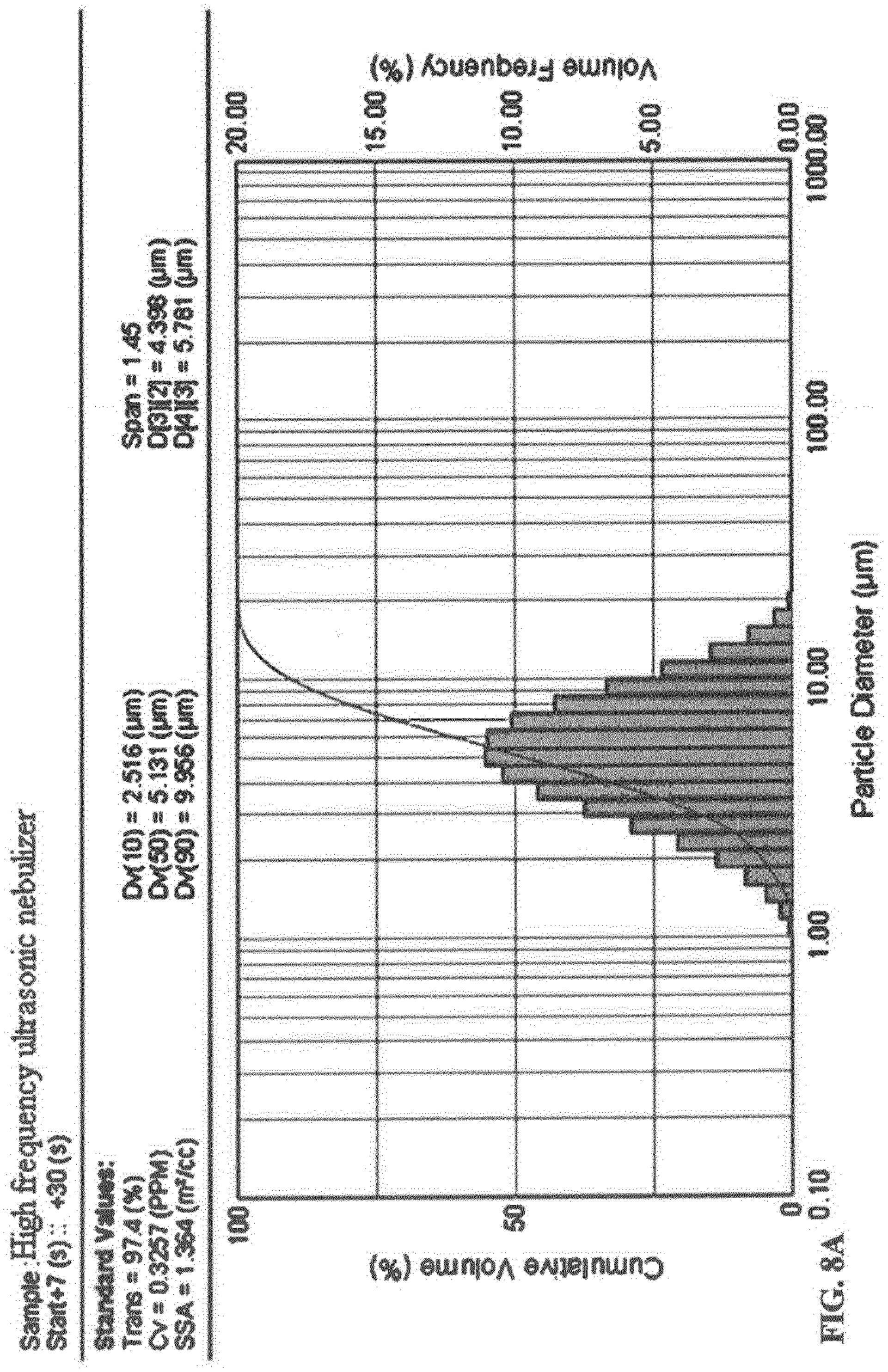
Figure 8B:
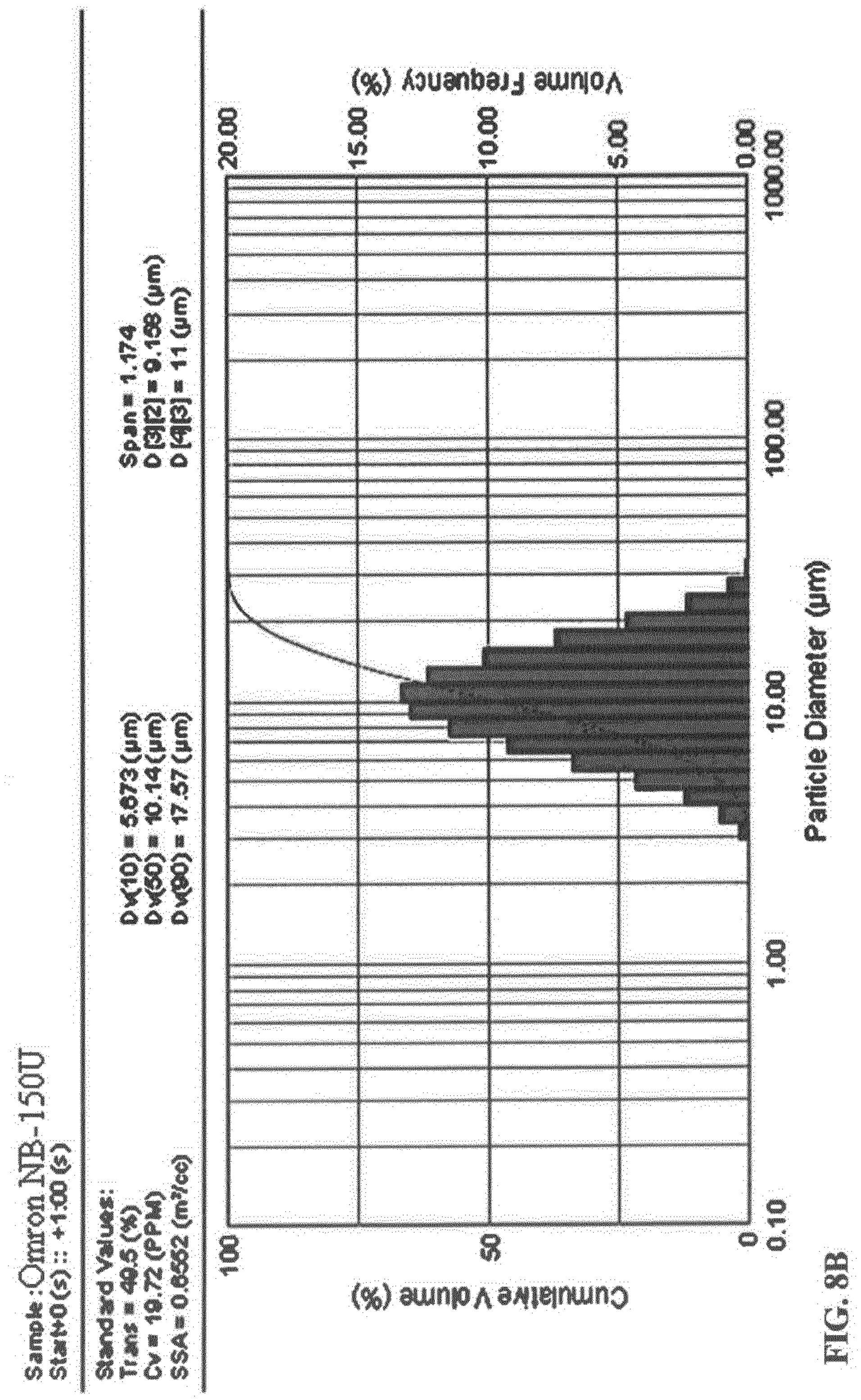
Figure 9A:
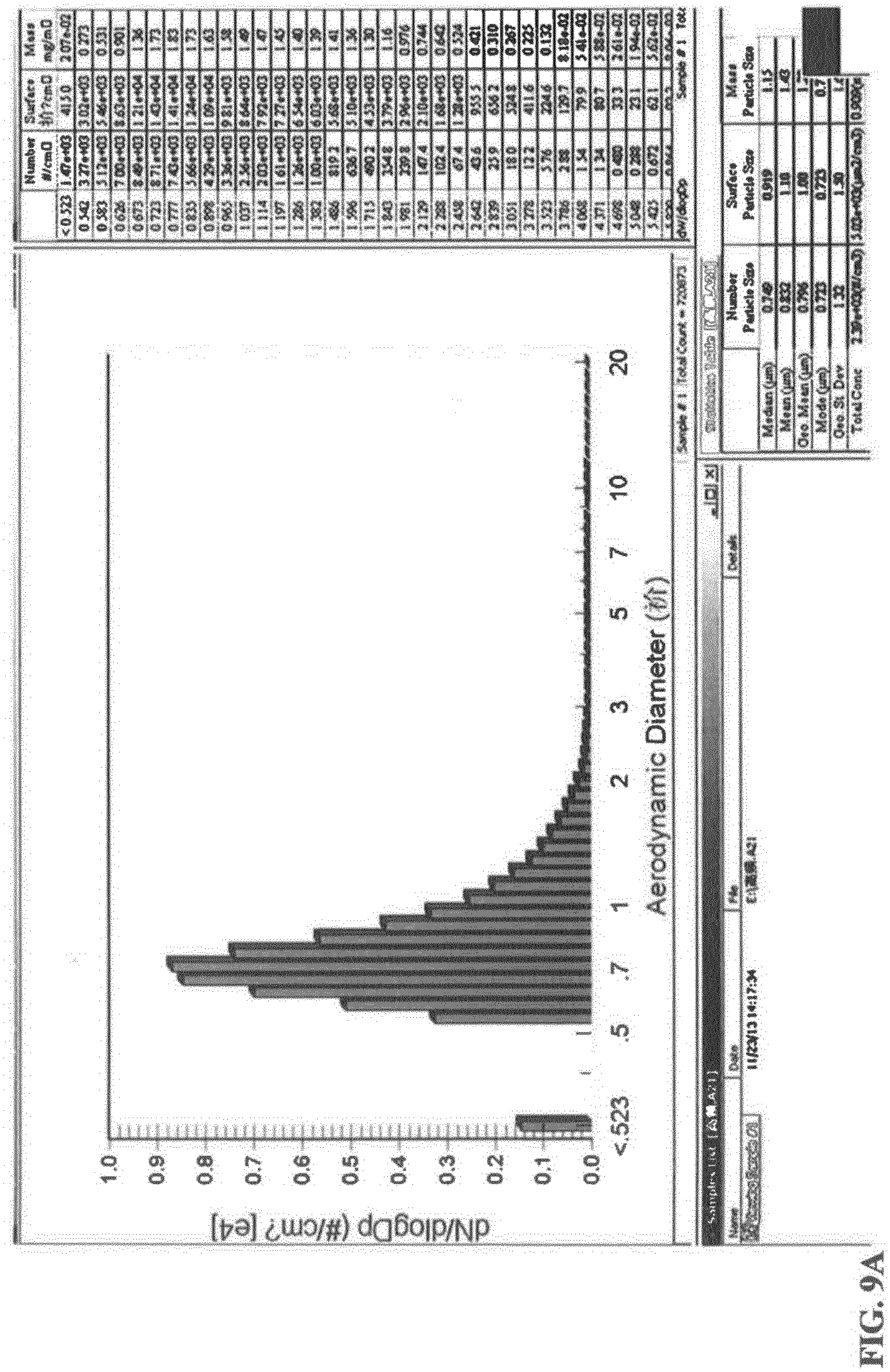
Figure 9B:
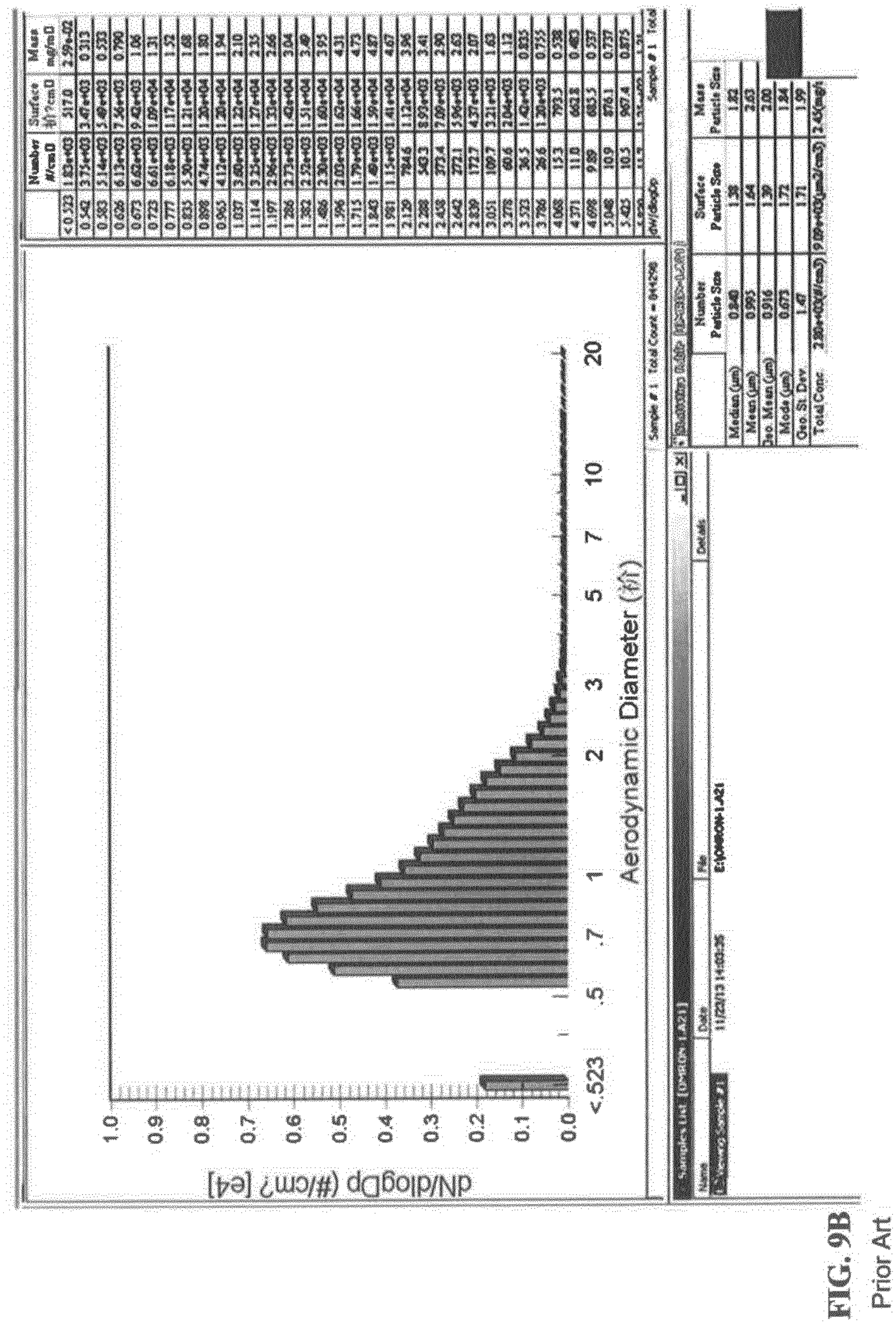

FIG. 1: Local section diagram of the handheld high frequency ultrasonic atomizing device for the present disclosure;

FIG. 2: Sketch view of the mouthpiece for the present disclosure;

FIG. 3: Sketch view of breather mask for the present disclosure;

FIG. 4: Upward view of piezoelectric ceramic transducer for the present disclosure;

FIG. 5: Downward view of piezoelectric ceramic transducer for the present disclosure;

FIG. 6: Section view of piezoelectric ceramic transducer for the present disclosure;

FIG. 7: Sketch view of distribution of different sizes atomized droplets in the respiratory tract after drug delivery;

FIGS. 8A and 8B: The atomizing effects diagram of the comparison between the drug delivery device for the present disclosure and current nebulizer device available in market by laser diffraction (LD) method;

FIGS. 9A and 9B: The atomizing effects diagram of the comparison between the drug delivery device for the present disclosure and current nebulizer device available in market by time-of-flight (TOF) aerodynamic particle size analysis.

wherein: 1—shell; 2—air inlet; 3—spray nozzle; 4—drug solution cup; 5—piezoelectric ceramic transducer; 6—blowing device; 7—circuit board; 8—battery; 9—hood for spray collection; 10—drugging hatch; 11—spray outlet; 12—air gallery; 13—piezoelectric main body; 14—upper electrode layer; 15—lower electrode layer; 16—protective layer of the upper electrode; 17—mouthpiece; 18—breather mask; 19—the first chamber; 20—the second chamber.

DESCRIPTION OF THE PREFERRED EMBODIMENTS

Hereinafter, the detailed information is elucidated combined with the preferred embodiments, so that it is much more easily to be understood by skilled technicians in the field upon the advantages and features for the present disclosure, and further clarify the boundaries of the claimed rights of the present disclosure.

This invention provides a portable/handheld high frequency ultrasonic nebulizer for whole respiratory tract drug delivery. FIG. 1 showed a preferred embodiment of whole respiratory tract drug delivery device in accordance with the present disclosure. The device (nebulizer) includes a shell 1 with an air inlet 2 at the bottom and a lid on the top of the mouth of the shell 1 with the open space, and a spray nozzle 3 on the lid (shell 1 and lid are two separated components for conveniently disassembly. They can also designed as a whole). The device (nebulizer) further includes a drug solution cup 4 with open mouth within the shell 1 and a hood 9 for mist collection upon the cup 4, and the bottom of the hood is located in the mouth of the cup 4 and further a gap between the outer layer of the hood 9 and the inner layer of the cup 4 formed, and the upper portion (or middle portion in some embodiments) of the hood 9 links tightly with the inner layer of the shell 1. Between the outer layer of the cup 4 and the inner layer of the shell 1 is the first chamber 19, the second chamber 20 lies between the outer layer of the hood 9 and the inner layer of the shell 1. A piezoelectric ceramic transducer 5 locates at the upper portion of the cup 4 and below the preset maximal liquid level. The cup layers 4 connects with the shell 1 through some linkers, where some air vents 12 existing around the linkers and/or layers of cup 4 above the maximal liquid level to link the first chamber 19 and the second chamber 20. Moreover, several spray outlets 11 on the top of the hood 9 connect with the spray nozzle 3 through vertical air vent. The device can also include a blowing device 6 located near the air inlet 2 for blasting air towards the spray nozzle 3, and can further include a circuit board 7 to control the spray link with the piezoelectric ceramic transducer 5. The piezoelectric main body 13 is made up of low power consumption materials, include the following major components (mass percent): lead tetraoxide ($Pb_3O_4$, 63.3-68.3%), zirconium dioxide ($ZrO_2$, 14.2-15.3%), titanium dioxide ($TiO_2$, 8.1-9.5%), strontium oxide (SrO, 4.6-5.2%), iron sesquioxide ($Fe_2O_3$, 1.5-1.8%), stannic oxide ($SnO_2$, 1.0-1.4%), and the following additive components (mass percent): manganese dioxide ($MnO_2$, 0.3-1.1%), cerium sesquioxide ($Ce_2O_3$, 0.5-0.8%), columbium pentoxide ($Nb_2O_5$, 0.4-0.8%), zinc oxide (ZnO, 0.3-0.7%).

In the present preferred embodiment for the present disclosure, a piezoelectric ceramic transducer 5 locates at the bottom of the cup 4 and beneath the maximal drug solution level, which promotes to high performance of the atomizing. The cup 4 will resonate along with the piezoelectric ceramic transducer 5, which producing ultrasonic wavelength and atomizing the solution in the cup 4 into droplets. It will be appreciated, however, that the piezoelectric ceramic transducer 5 can be set at the side wall of the cup 4 or other locations, which will not limited by the present embodiment, which is just as an example.

In this embodiment, the wall of the cup 4 connects with the shell 1 through linkers, where air vents 12 around the linkers to link the first chamber 19 and the second chamber 20. Through the vents 12, the two chambers are connected and the airflow generated by the blowing device goes through from the first chamber 19 to the second chamber 20. Further the airflow is driven from the gap between the bottom out wall of the hood 9 and inside wall of the cup 4 into the hood 9, so that the drug droplets arising from the liquid level in the drug cup 4 flow upward inside the hood 9 and finally discharged through the spray outlet 11. Since all the detailed settings are easily understood by a technician in the art, any settings with similar functions with the vents should be under the protection scope of the present disclosure. For example, some vents can be located at the wall of the cup 4 and accordingly, in this case the vents should be higher than the maximal top liquid level to gain the airflow directly. Or the combination of these two vents can be used in an embodiment. The upper portion of the hood 9 and the shell 1 connect tightly, the top of where distributes spray outlets 11 (The headpiece of the hood 9 can be a natural part of the hood 9, or any other separate covers with spray outlets) connects with the spray nozzle 3 through vertical air vent. More specifically, the number of spray outlets 11 is not limited and distributed circumferentially with specific intervals, which blocks the bigger droplets and let the smaller droplets out of the spray nozzle 3 freely.

The present disclosure further includes an atomizing control circuit board 7 connecting with the piezoelectric ceramic transducer 5, and a battery pack 8 supplying power for the circuit board and/or blowing device. The piezoelectric ceramic transducer 5 comprises piezoelectric main body 13 whose surface is arranged with cavities, the upper electrode layer 14 and the lower electrode layer 15. The upper electrode layer 14 comprises a covered part upon the piezoelectric main body 13's upper surface, and an extended part extending from the covered part to the piezoelectric main body 13's lower surface through downward bending to enclose the edges of the piezoelectric main body 13. The lower electrode layer 15 covers upon the piezoelectric main body 13's lower surface, whose edges are kept from a proper distance to the extended part of the upper electrode layer 14. The upper electrode layer 14 away from the piezoelectric main body 13's upper surface comprises a protective layer 16 to protect the upper electrode. The piezoelectric main body 13 is made up of lower power dissipation materials. As can be envisioned for the present disclosure, the drug solution in the cup 4 is driven by high frequency resonance to form an atomizing zone, whose space is connected with the cavity inside of the hood 9, so the atomizing droplets will flow from the hood 9, the spray outlets 11 upon the hood 9 to the spray nozzle 3 and then conveniently used by patients. In this embodiment, the blowing device is a fan, the first chamber 19 and the second chamber 20 lies respectively between the outer layer of the cup 4 and the inner layer of the shell 1, and between the outer layer of the hood 9 and the inner layer of the shell 1, which forms a channel for fluid circulation. The fan 6 provides airflow to the inner space of the device through the air inlet 2, and then the airflow will flow to the spray nozzle 3 through the first chamber 19 between the cup 4 and the inner layer of the shell 1, further through the vents 12 located on the linkers around drug cup 4 and shell 1 go into the second chamber 20 between the outer layer of the hood 9 and the inner layer of the shell 1. Additionally, the upper portion of the hood 9 connects tightly with the shell 1, the lower portion is located in the open of drug cup 4, where the a gap exists between the outer layer of the hood 9 and the inner layer of the shell 1, so that the airflow from the air gap can be blown into the lower inner space of the hood 9 with upward flow, and further the droplets in the drug cup 4 will be driven upwardly. Furthermore, the droplets are expelled through the spray outlet 11 on the top of the hood 9 and the spray nozzle 3 on the lid, and then delivered into the respiratory tracts and pulmonary alveoli through mouthpiece 17 connecting with the spray nozzle 3 or through breather mask 18. That is, an airflow channel is formed from the air inlet 2, the vents 12, the first chamber 19, the second chamber 20, and the spray outlet 11 to the spray nozzle 3, through which the airflow promoting resonance generated from the piezoelectric ceramic transducer 5, pushing the atomized droplets expelled through the spray nozzle 3 into the patients/users.

The materials of the piezoelectric main body for the present disclosure include the following major components:

63.3% weight percentage lead tetraoxide ($Pb_3O_4$);
14.7% weight percentage zirconium dioxide ($ZrO_2$);
8.7% weight percentage titanium dioxide ($TiO_2$);
4.9% weight percentage strontium oxide (SrO);
1.7% weight percentage iron sesquioxide ($Fe_2O_3$);
1.2% weight percentage stannic oxide ($SnO_2$);
and following additive components:
0.7% weight percentage manganese dioxide ($MnO_2$);
0.6% weight percentage cerium sesquioxide ($Ce_2O_3$);
0.7% weight percentage columbium pentoxide ($Nb_2O_5$);
0.5% weight percentage zinc oxide (ZnO).

In the present embodiment, the upper electrode layer 14 and the lower electrode layer 15 of the piezoelectric ceramic transducer 5 are gold electrode layers, and the protective layer 16 of the upper electrode is ceramic protection layer. The device further includes a drugging hatch 10 set upon the shell 1 for connecting medicine bottle or filling drug solution, and an open hatch located at the hood 9's wall corresponding to the drugging hatch 10 of the shell 1. The drugging hatch 10 and the aforementioned open hatch are used for installing the external medicine bottle or filling drug solution into the drug cup 4.

The device of the present embodiment further includes a battery pack 8 with the voltage between 1.5 v-4.5 v to supply power to the circuit board 7 and/or the blowing device 6. The circuit board 7 drives the piezoelectric ceramic transducer 5 by the battery pack 8, or through connection port to gain external voltages. In any cases, only 1.5-10 v, preferably 1.5-4.5 v of the power is needed. Namely, by using the curved surface structural designing transducer of the present application made up of low power consumption, only several volts generated from ordinary battery is sufficient to drive the transducer. The atomizing control circuit board 7 is arranged inside the shell 1, where a connection port is installed to supply power to the circuit board 7 and/or the blowing device 6. As shown in FIG. 2 and FIG. 3, the device also includes a mouthpiece 17 or a breather mask 18 linked to the spray nozzle 3 through some linkers, whose size and shape are exactly well matched with the spray nozzle 3. The linker can directly snap into and connect tightly with the spray nozzle 3 by forces of friction contact surface, which impels the whole atomizing droplets with appropriate sizes ejecting uniformly through the mouthpiece 17 or the breather mask 18.

A whole set of cavities is distributed on the surface of the piezoelectric main body 13 with the shape of circular, oval, square, rectangular, diamond, triangle or theirs combinations. The longitudinal section of the piezoelectric ceramic transducer 5 is arc-shaped in the main. FIG. 4 shows the upward view of the piezoelectric ceramic transducer 5, and FIG. 5 is the downward view of the piezoelectric ceramic transducer 5, and FIG. 6 shows the longitudinal section diagram of the piezoelectric ceramic transducer 5.

Referring now to FIG. 5, the shape of the piezoelectric ceramic transducer 5 in this embodiment is circular curved surface structure, or partially circular curved or even discontinuous multiple circular curved structures. The radian of the arc is an arbitrary value between 0-$\pi$. For example, the radian value of the transducer is $\pi/4$, equivalent to the circular arc corresponding to a 45° radius angle. In another example, both ends of the transducer are of planar structures, while the middle is a semi-circle curved structure.

As shown in the figures, the piezoelectric ceramic transducer 5 for the present disclosure includes piezoelectric main body 13 as the major component, whose surface is arranged with some cavities with specific sizes and shapes. The shape, quantity, density and depth of these cavities include but not limited to the following conditions: all the cavities with any specific quantity (such as 100 or 200) on a transducer surface are circular; A part of cavities (appropriate quantity) on a transducer surface are circular, other cavities (appropriate quantity) are square; A part of cavities (appropriate quantity) on a transducer surface are oval, some (appropriate quantity) are diamond, the rest others (appropriate quantity) are irregular polygons. Further, the density distribution of the cavities on a transducer can be uniformly, or can be non-uniformly distributed with some areas are more dense than other areas. Additionally, the density of cavities on the surface of a piezoelectric ceramic transducer can be an appropriate value, which is dependent on the preparation process and application requirements.

The present disclosure is a high frequency ultrasonic nebulizing device for whole respiratory tract drug delivery with low power consumption. It is characterized with much smaller droplets generation through high frequency ultrasound. The main body of the diameter of the droplets generated in the present device falls in the scope of 2-4 micrometer (μm) which can be delivered into the lower respiratory tract/pulmonary alveoli; whereas a small part of relatively bigger droplets will be distributed into the upper and middle respiratory tracts. During inhaled drug delivery, the distribution position of the droplets in the tracts is highly dependent on the sizes of the droplets, as shown in FIG. 7. The bigger of the droplets is, the more possibility it distributed in upper respiratory tract. When the size of the droplets decreased, it will be distributed into the lower respiratory tract/pulmonary alveoli.

The droplets generated by the drug delivery device of the present disclosure are relatively smaller than droplets generated from similar products, and mainly enter into the lower respiratory tract via inhalation. FIG. 8 showed the diameter of the droplets measured by laser diffraction (LD) particle sizing technique by Spraytec Laser Diffraction System from Malvern Instruments (Spraytec, Malvern, UK), which shows the difference of the of droplets in size between the present invested nebulizer and a nebulizer made of Omron (refer to D50 distribution). The median diameter of the droplets generated by the present invented handheld high frequency ultrasonic nebulizer for whole respiratory tract drug delivery is 5.13 micrometer (μm) (FIG. 8A), while the median diameter of the droplets generating by Omron nebulizer is 10.14 micrometer (μm) (FIG. 8B). Alternatively, when the diameter of the droplets is measured by Aerodynamic Particle Sizer Spectrometer (Model APS-3321) using time-of-flight method, and the sizes of the droplets are compared between the present invented nebulizer and a nebulizer made of Omron (refer to mean mass distribution). The median diameter of the droplets generated by the present invented high frequency handheld ultrasonic nebulizer for whole respiratory tract drug delivery is 1.43 micrometer (μm) (FIG. 9A), while the median diameter of the droplets generating by Omron nebulizer is 2.63 micrometer (μm) (FIG. 9B). The results from the two detection methods show that the droplets generated by present invented handheld high frequency ultrasonic nebulizer for whole respiratory tract drug delivery are about 50% smaller than the droplets generating by Omron nebulizer.

Therefore, this handheld high frequency ultrasonic device for whole respiratory tract drug delivery has the advantages of low power consumption, portable and low manufacturing costs, as well as much smaller atomizing droplets generated. All of the characters makes the present invented device (nebulizer) very suitable for efficiently delivering drugs into the whole respiratory tract, with broader applications in the futures.

Hereinbefore, the present invented particular nebulizer, system and method as herein shown and disclosed in detail is fully capable of obtaining the objects and providing the advantages herein before stated, it is to be understood that it is merely illustrative of the presently preferred embodiments of the invention, many other possible modifications and variations can be made without departing from the spirit and scope of the invention claimed.

The invention claimed is:

1. A handheld high frequency ultrasonic atomizing device for delivering drugs to a person's whole respiratory tract, which comprises:
   - a shell with open space, which includes an air inlet on the bottom;
   - a lid on an upper mouth of the shell;
   - a spray nozzle on the lid;
   - a drug solution cup with an open mouth and a hood above the cup located within the shell, a bottom of the hood being located within the open mouth of the cup, an upper portion of the hood linking tightly with an inner surface of the shell, with a gap between an outer surface of the hood and an inner surface of the cup, the device including a first chamber lying between the outer surface of the cup and the inner surface of the shell and a second chamber lying between the outer surface of the hood and the inner surface of the shell;
   - a piezoelectric ceramic transducer located in the cup and below a preset maximal liquid level, the cup linking with the shell through a linker;
   - a plurality of air vents for connecting the first chamber and the second chamber, the plurality of air vents being provided on the linker and/or an upper part of the cup which is above the preset maximal liquid level;
   - several spray outlets being provided on a top of the hood and connected with the spray nozzle;
   - a blowing device located near the air inlet for blasting air towards the spray nozzle; and
   - a circuit board connecting with the piezoelectric ceramic transducer, wherein:
   - the piezoelectric ceramic transducer comprises a piezoelectric main body, an upper electrode layer and a lower electrode layer covered upon the piezoelectric main body;
   - the upper electrode layer comprises a covered part upon an upper surface of the piezoelectric main body, and a curved part extending downward from the covered part to a lower surface of the piezoelectric main body to enclose edges of the piezoelectric main body;
   - the lower electrode layer covered upon the lower surface of the piezoelectric main body, with an edge kept at a distance to the curved part of the upper electrode layer;
   - the upper electrode layer is covered by a protective layer;
   - the piezoelectric main body is made up of low power dissipation materials, whose major components include:
     - 63.3-68.3% weight percentage lead tetraoxide;
     - 14.2-15.3% weight percentage zirconium dioxide;
     - 8.1-9.5% weight percentage titanium dioxide;
     - 4.6-5.2% weight percentage strontium oxide;
     - 1.5-1.8% weight percentage iron sesquioxide; and
     - 1.0-1.4% weight percentage stannic oxide; and
   - the piezoelectric main body further includes following additive components:
     - 0.3-1.1% weight percentage manganese dioxide;
     - 0.5-0.8% weight percentage cerium sesquioxide;
     - 0.4-0.8% weight percentage columbium pentoxide; and
     - 0.3-0.7% weight percentage zinc oxide.

2. The handheld high frequency ultrasonic atomizing device as recited in claim 1, wherein:
   - a plurality of cavities are set on the upper surface and the lower surface of the piezoelectric main body, whose shapes include but not limited to circular, oval, square, rectangle, prismatic, triangle and their combinations.

3. The handheld high frequency ultrasonic atomizing device as recited in claim 1, wherein
   - said several spray outlets are evenly arranged along a circumferential direction.

4. The handheld high frequency ultrasonic atomizing device as recited in claim 1, wherein
   - a longitudinal section of the piezoelectric ceramic transducer is shaped as an arc, which travels through an angle between 0 to $\pi$ radians.

5. The handheld high frequency ultrasonic atomizing device as recited in claim 1, wherein
   - a plurality of ultrasonic frequencies of the piezoelectric ceramic transducer are between 1.0 to 10 mega hertz.

6. The handheld high frequency ultrasonic atomizing device as recited in claim 1, wherein
   - diameters of atomized drug particles formed by the piezoelectric ceramic transducer are between 0.1 to 5 micrometers.

7. The handheld high frequency ultrasonic atomizing device as recited in claim 1, wherein:
   - the upper electrode layer and the lower electrode layer of the piezoelectric ceramic transducer are a gold electrode or a silver electrode, and
   - the protective layer is an alloy coating or a ceramic protection layer.

8. The handheld high frequency ultrasonic atomizing device as recited in claim 1, further comprising a battery to supply power to the circuit board and/or the blowing device.

9. The handheld high frequency ultrasonic atomizing device as recited in claim 1, wherein a voltage of the battery is between 1.5 to 10 Volts.

10. The handheld high frequency ultrasonic atomizing device as recited in claim 1, wherein:
    - the circuit board is placed inside the shell, with a port of wiring on the shell for the circuit board and/or the blowing device connect with a power.

11. The handheld high frequency ultrasonic atomizing device as recited in claim h wherein:
    - a drugging hatch is set upon the shell for connecting with a medicine bottle or filling a drug solution, and
    - an open hatch located at the spray hood's wall corresponds to the drugging hatch of the shell.

12. The handheld high frequency ultrasonic atomizing device as recited in claim 1, further comprising a mouthpiece or a breather mask linked to the spray nozzle.

* * * * *